(12) United States Patent
Saha et al.

(10) Patent No.: US 11,364,231 B2
(45) Date of Patent: Jun. 21, 2022

(54) METHODS OF TREATING RADIATION INDUCED GASTROINTESTINAL SYNDROME (RIGS) AND RELATED DISEASE STATES USING YEL002/BCN057

(71) Applicants: University of Kansas, Lawrence, KS (US); BCN Biosciences L.L.C., Inglewood, CA (US)

(72) Inventors: Subhrajit Saha, Overland Park, KS (US); Andrew J. Norris, Los Angeles, CA (US)

(73) Assignees: University of Kansas, Lawrence, KS (US); BCN Biosciences L.L.C., Inglewood, CA (US)

( * ) Notice: Subject to any disclaimer, the term of this patent is extended or adjusted under 35 U.S.C. 154(b) by 0 days.

(21) Appl. No.: 16/870,864

(22) Filed: May 8, 2020

(65) Prior Publication Data

US 2020/0368222 A1    Nov. 26, 2020

Related U.S. Application Data

(63) Continuation of application No. 16/159,502, filed on Oct. 12, 2018, now abandoned.

(60) Provisional application No. 62/571,721, filed on Oct. 12, 2017.

(51) Int. Cl.
*A61K 31/4704* (2006.01)
*A61K 45/06* (2006.01)

(52) U.S. Cl.
CPC .......... *A61K 31/4704* (2013.01); *A61K 45/06* (2013.01)

(58) Field of Classification Search
CPC .................................................. A61K 31/4704
See application file for complete search history.

(56) References Cited

U.S. PATENT DOCUMENTS

| 9,045,474 B2* | 6/2015 | Schiestl | A61K 31/00 |
| 2013/0231518 A1* | 9/2013 | Schiestl | A61P 39/02 |
| | | | 600/1 |

* cited by examiner

*Primary Examiner* — Kevin E Weddington
(74) *Attorney, Agent, or Firm* — Entralta P.C.; James F. Fleming; Peter D. Weinstein

(57) ABSTRACT

The present disclosure is directed to method of treatment for treating or ameliorating various conditions caused by radiation exposure such as RIGS, enteritis, oral mucositis, mucositis, and proctitis by the administration of a compound Yel002/BCN057 or an analog thereof.

6 Claims, 20 Drawing Sheets

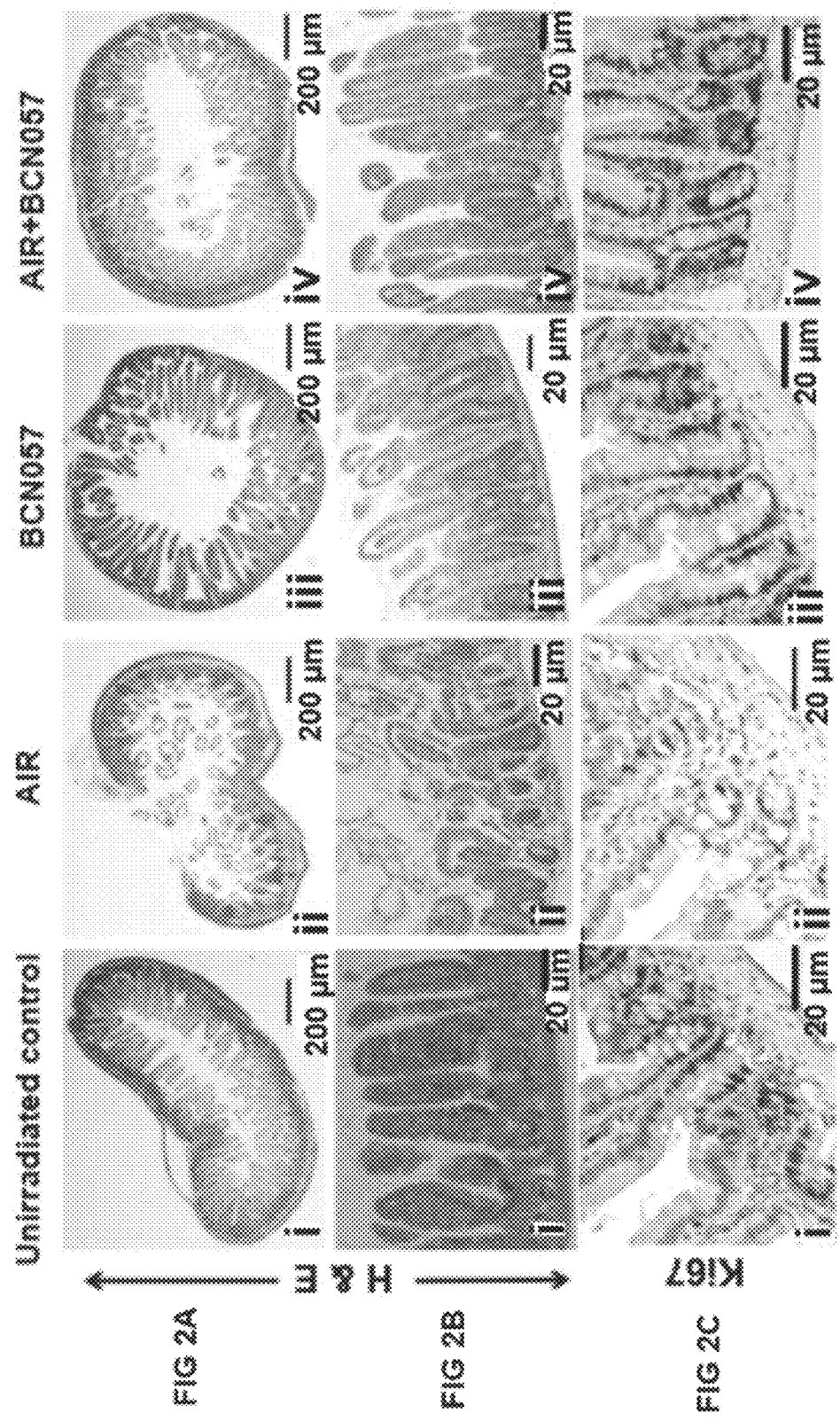

METHODS OF TREATING RADIATION INDUCED GASTROINTESTINAL SYNDROME (RIGS) AND RELATED DISEASE STATES USING YEL002/BCN057

CROSS-REFERENCE TO RELATED APPLICATIONS

This application is a continuation of patent application Ser. No. 16/159,502 and claims the benefit of U.S. provisional patent application Ser. No. 62/571,721, filed Oct. 12, 2017, and entitled "METHODS OF TREATING RADIATION INDUCED GASTROINTESTINAL SYNDROME (RIGS) AND RELATED DISEASE STATES USING YEL002/BCN057", whereby the contents of the aforementioned application are incorporated herein by reference.

REFERENCE TO GOVERNMENT RIGHTS

This disclosure was made with government support under grant number DK096032 awarded by the National Institutes of Health. The government has certain rights in the disclosure.

BACKGROUND

The risk of large populations encountering radiation exposure is real and growing due to the proliferation of rogue non-state actors, political instability resulting in potential access of nuclear weapons by terrorist, and by natural disaster as evidenced by the release of radioactive material from the Fukushima nuclear power plant in early 2011. Total body exposure to radiation results acute radiation syndromes describing a clinical condition with multi organ syndrome. Radiation doses less than 8 Gy primarily develops hematopoietic injury and can be treated with supportive care with antibiotics, hydration and bone marrow transplantation. Doses of more than 10 Gy primarily leads to gastrointestinal injury resulting diarrhea, dehydration, sepsis and intestinal bleeding with eventual mortality within 10 to 15 days post-exposure. High doses of radiation induces the loss of intestinal stem cells (ISC) and thereby impairs epithelial regeneration. The damaged intestinal epithelium significantly reduces the mucosal integrity and promotes systemic influx of bacterial pathogens, resulting sepsis and death. These lethal gastrointestinal symptoms after radiation exposure are collectively known as radiation-induced gastrointestinal syndrome (RIGS).

There are few FDA approved radio-protectors able to ameliorate RIGS if applied prior to radiation exposure. However, no drugs are available which can mitigate RIGS when administered hours or days post irradiation. Considering the logistical barrier and unavoidable delay to treat victims in large casualty settings there is a tremendous need of such therapeutic measures which can be effective even if started days after radiation incident.

Dose dependent radiation damage to the intestinal stem cell is the primary cause of RIGS. It has been reported previously that inhibition of radiation induced ISC loss mitigates RIGS. This recent study demonstrated that extracellular vesicle (EV) mediated delivery of WNT rescues ISCs from radiation toxicity and induces intestinal epithelial repair with the activation of WNT-β catenin signaling. Wnt/β-catenin signaling plays a major role in ISC self-renewal and proliferation and thereby maintenance of intestinal epithelial homeostasis and repair. WNT ligands bind to LRP5/6 and Frizzled co-receptors present on epithelial crypt cells, leading to β-catenin stabilization and nuclear translocation where it binds to the nuclear transcription factor TCF4 to drive a gene-expression program that supports stem cell maintenance, proliferation and differentiation. Activation of WNT/β-catenin signaling is also crucial for crypt regeneration following injury. Several reports, have demonstrated that Respondin 1 (RSPO1), an ISC growth factor and LGR5 receptor agonist, activates WNT/βcatenin pathway to repair and regenerate the intestine following chemo-radiation-induced injury. DKK1, a negative regulator WNT/β-catenin pathway, impairs the RSPO1-induced intestinal regeneration. LGR5 receptor is associated with Frizzled/Lrp Wnt receptor complex. Genetic deletion of Lgr5 in mouse intestinal inhibits Rspo1 mediated signaling but can be rescued by Wnt pathway activation.

The present disclosure demonstrates that the small molecular agent YEL002, also known as BCN057, (3-[(Furan-2-ylmethyl)-amino]-2-(7-methoxy-2-oxo-1,2-dihydro-quinolin-3-yl)-6-methyl-imidazo[1,2-a]pyridin-1-ium) mitigates RIGS and improves survival when applied after lethal dose of radiation exposure, preferably within or after 24 hours of exposure. BCN057 has strong WNT activity as demonstrated in TCF/LEF reporter assay.

In an ex-vivo crypt organoid model developed from human and mice intestinal epithelium, BCN057 rescued ISCs from radiation toxicity and induced epithelial repair with the activation Wnt/βcatenin signaling. However, BCN057 did not show any radio-protective effect in tumor tissue. Taken together these observations indicate that BCN057 is an agonist of Wnt/βcatenin signaling and mitigate radiation induced intestinal injury by accelerating repair and regeneration of ISCs. Thus, BCN057 is also useful in mitigating radiation-induced syndromes related to RIGS and ISC rescue, such as oral mucositis, mucositis, enteritis, and proctitis. These syndromes are also often an unwanted side-effect of radiation therapy for cancer and can be treated using BCN057.

SUMMARY OF THE DISCLOSURE

In one aspect, disclosed herein is a method of treating radiation induced gastrointestinal syndrome (RIGS) in a subject in need thereof, the method comprising the step of administering to the subject a therapeutically effective amount of a compound of Formula I:

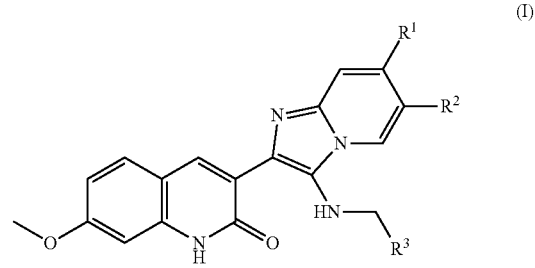

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

In some embodiments, disclosed herein is a method of treating radiation induced gastrointestinal syndrome (RIGS) in a subject in need thereof, the method comprising the step of administering to the subject a therapeutically effective amount of a compound of Formula IA, or an analog thereof.

In another aspect, disclosed herein is a method of treating radiation induced mucositis in a subject in need thereof, the method comprising the step of administering to the subject a therapeutically effective amount of a compound of Formula I:

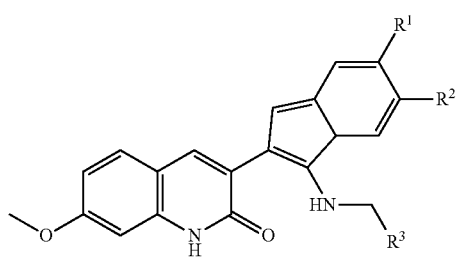

(I)

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

In some embodiments, disclosed herein is a method of treating radiation induced mucositis in a subject in need thereof, the method comprising the step of administering to the subject a therapeutically effective amount of a compound of Formula IA or an analog thereof.

In another aspect, disclosed herein is a method of treating radiation induced oral mucositis in a subject in need thereof, the method comprising the step of administering to the subject a therapeutically effective amount of a compound of Formula I:

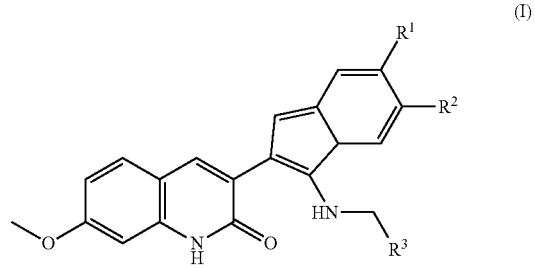

(I)

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

In some embodiments, disclosed herein is a method of treating radiation induced oral mucositis in a subject in need thereof, the method comprising the step of administering to the subject a therapeutically effective amount of a compound of Formula IA or an analog thereof.

In another aspect, disclosed herein is a method of treating radiation-induced proctitis in a subject in need thereof, the method comprising the step of administering to the subject a therapeutically effective amount of a compound of Formula I:

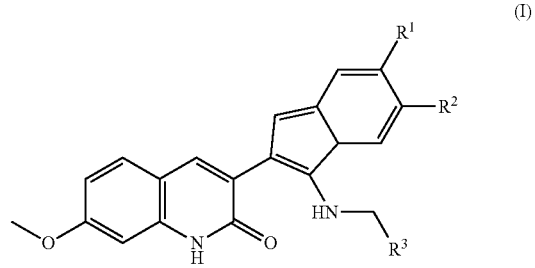

(I)

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

In another embodiment, disclosed herein is a method of treating radiation-induced proctitis in a subject in need thereof, the method comprising the step of administering to the subject a therapeutically effective amount of a compound of Formula IA, or an analog thereof.

In another embodiment, disclosed herein is a method of treating radiation induced enteritis in a subject in need thereof, the method comprising the step of administering to the subject a therapeutically effective amount of a compound of Formula I:

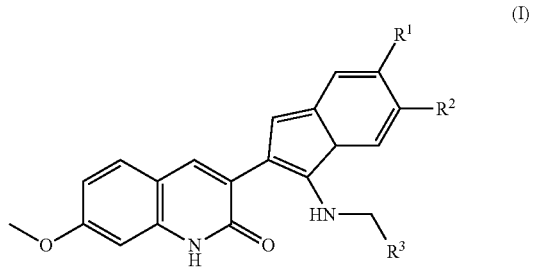

(I)

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

In another embodiment, disclosed herein is a method of treating radiation induced enteritis in a subject in need thereof, the method comprising the step of administering to the subject a therapeutically effective amount of a compound of Formula IA, or an analog thereof.

In another embodiment, disclosed herein is a method of treating radiation induced hematopoietic syndrome in a subject in need thereof, the method comprising the step of administering to the subject a therapeutically effective amount of a compound of Formula I:

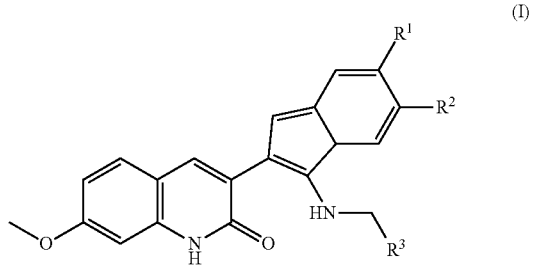

(I)

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

In another embodiment, the disclosure provides a method of treating radiation induced hematopoietic syndrome in a subject in need thereof, the method comprising the step of administering to the subject a therapeutically effective amount of a compound of Formula IA, or an analog thereof.

In another embodiment, the compound is administered to the subject within 48 hours of the radiation exposure. In one embodiment, the compound is administered to the subject after 24 hours of the radiation exposure.

In another embodiment, the analog is selected from the group consisting of Formula IB-H. In one embodiment, the compound is Formula IA.

In another embodiment, the subject received radiation therapy.

BRIEF DESCRIPTION OF THE DRAWINGS

FIG. 1A. Schematic diagram demonstrating the AIR exposure field and BCN057 Treatment schema. A 3 cm area of the mice containing the GI was irradiated (irradiation field), thus shielding the upper thorax, head and neck as well as lower and upper extremities, protecting a significant portion of the bone marrow, thus inducing predominantly RIGS. Mice exposed to AIR were treated with BCN057 (s.c.) (150 mg/kg of body weight) at 24 hrs post irradiation and continued up to day 8 (single dose/day).

FIG. 1B. Kaplan Meier survival analysis of C57B16 mice (n=25/group) receiving vehicle, BCN057 or no treatment at 24 hrs post AIR (14Gy and 15Gy) and continued up to day 8. Mice receiving BCN057 after 14Gy or 15Gy AIR demonstrated 80% and 60% survival respectively and they continued to survive beyond 60 days without any symptom of gastroenteritis or any other health complications whereas mice receiving vehicle or no treatment post AIR died within 15 days post AIR (p<0.0003 and p<0.0004 respectively Log-rank (Mantel-Cox) test). BCN057 or vehicle do not confer any toxicity to normal mice.

FIG. 1C. Kaplan Meier survival analysis of C57B16 mice (n=25/group) exposed to PBI (BM40). Head & Neck and upper extremities were shielded to spare 40% of bone marrow. Mice receiving BCN057 at 24 hrs post PBI demonstrated 70% survival compared to untreated control (p<0.0003 Log-rank (Mantel-Cox) test).

FIGS. 2-6: BCN057 induces repair and regeneration of irradiated intestinal epithelium FIG. 2. [[a]] FIG. 2A. HE stained representative cross section of jejunum from C57B16 mice treated with BCN057 at 24 hrs post AIR. Note restitution of epithelium in mice receiving BCN057 compared to irradiated control; [[b]] FIG. 2B. HE stained representative transverse section of jejunum from C57B16 mice treated with BCN057 at 24 hrs post AIR. Note, restitution on crypt villus structure in BCN057 treated mice. However, irradiated untreated mice showed significant loss of crypts along with villi denudation;

and [[c]] FIG. 2C. Representative Ki67 immunohistochemistry of mice jejunal sections. Note increase in crypt cell proliferation in mice receiving BCN057 at 24 hrs after AIR (iii) compared to AIR control (ii).

Figure 3:
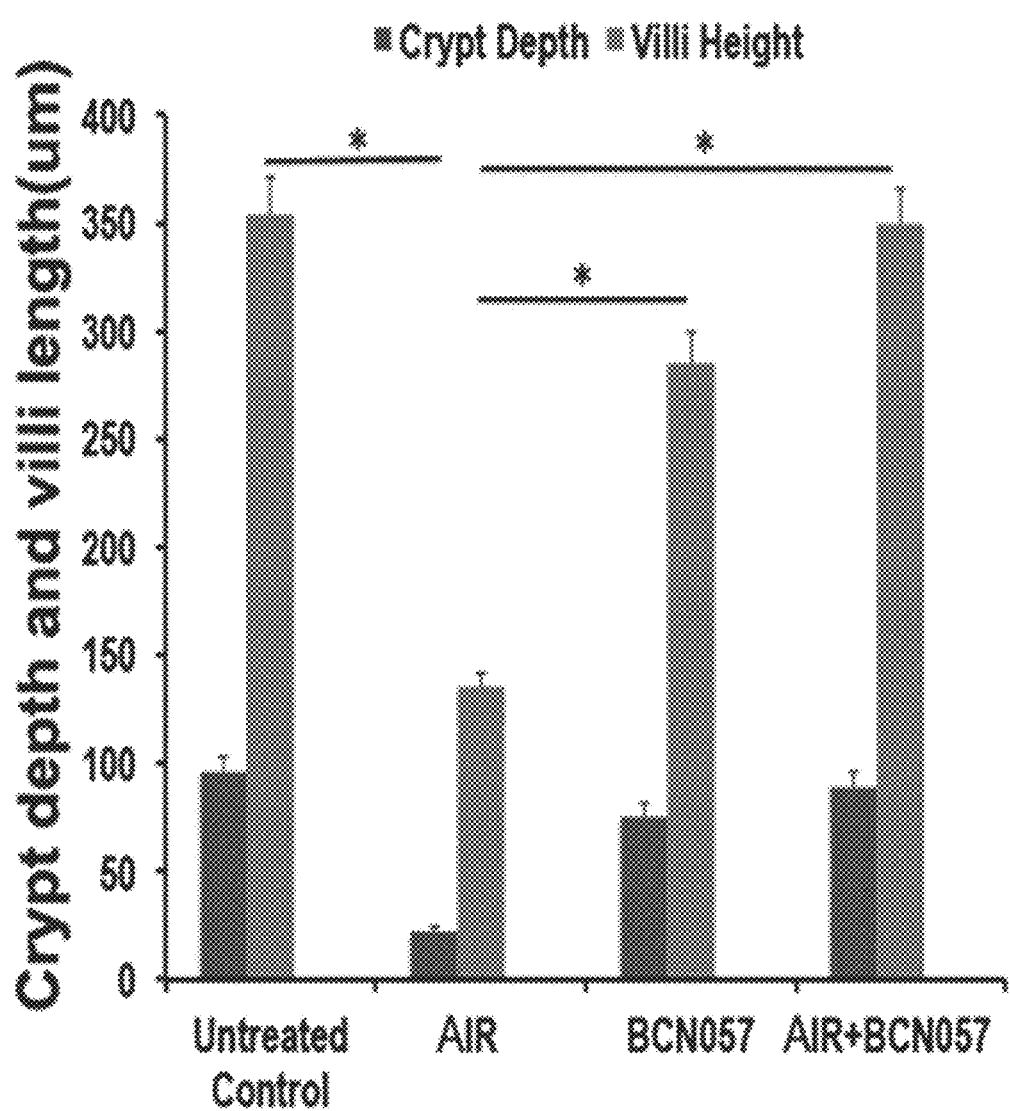

FIG. 3. Histogram showing Crypt Depth villi length. Irradiated mice receiving BCN057 at 24 hrs after AIR demonstrated increase in Crypt Depth villi length, number of crypt and % of Ki67 positive crypt cells compared to irradiated control.

Figure 4:
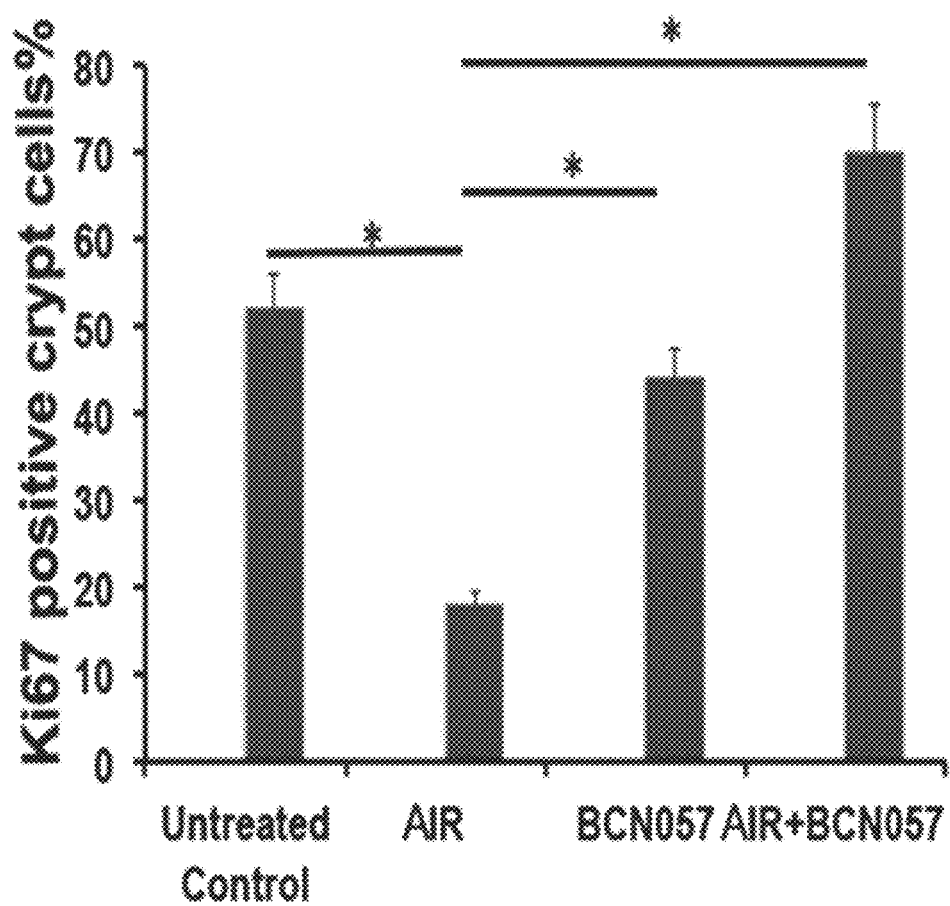

FIG. 4. Histogram showing % of Ki67 positive crypt cell in jejunum. Irradiated mice receiving BCN057 at 24 hrs after AIR demonstrated increase in Crypt Depth villi length, number of crypt and % of Ki67 positive crypt cells compared to irradiated control.

Figure 5:
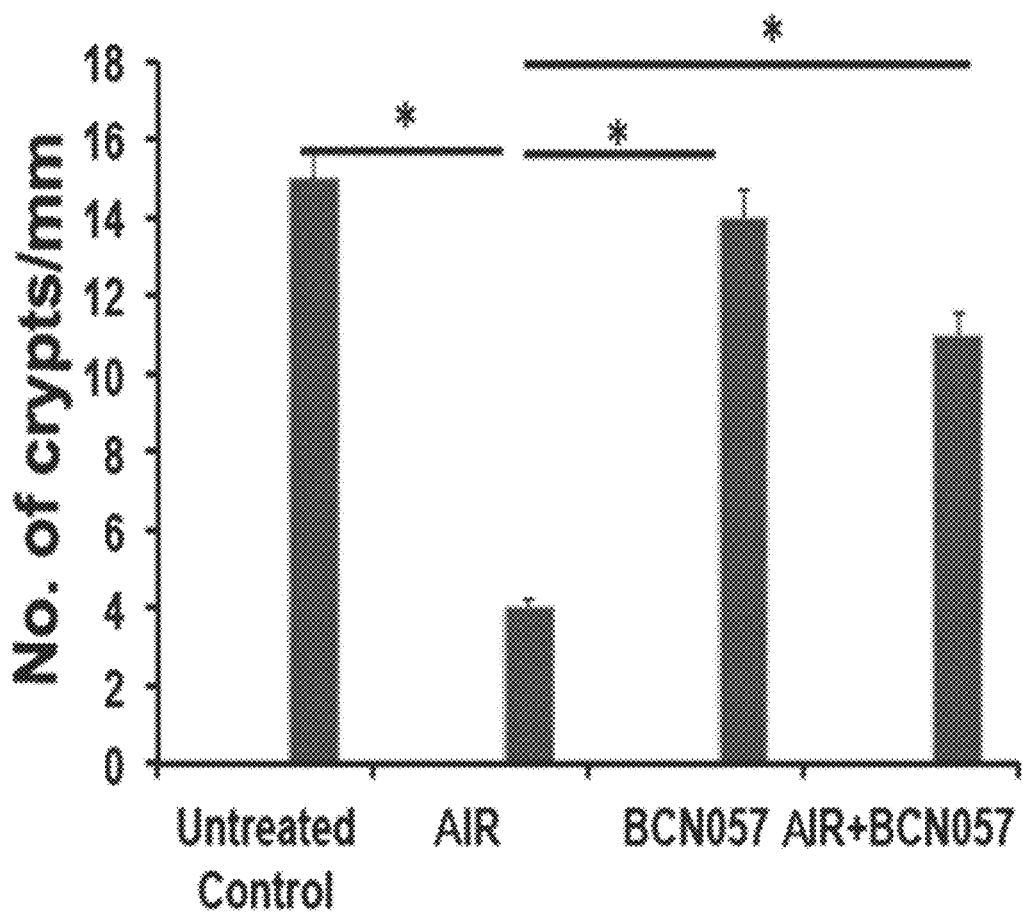

FIG. 5. Histogram showing number of crypt in jejunum. Irradiated mice receiving BCN057 at 24 hrs after AIR demonstrated increase in Crypt Depth villi length, number of crypt and % of Ki67 positive crypt cells compared to irradiated control.

Figure 6:
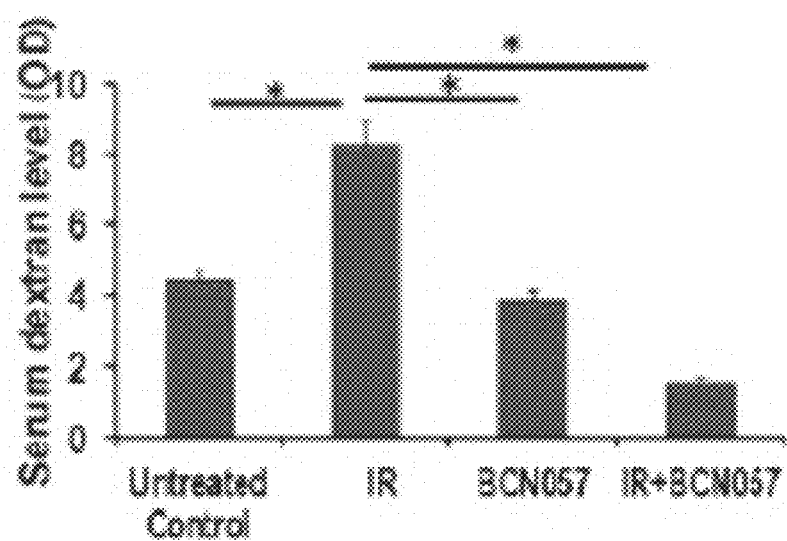

FIG. 6. Histogram demonstrating serum dextran level in C57B16 mice exposed to AIR and then treated with/without BCN057. Mice receiving BCN057 treatment demonstrated lower serum dextran level thereby suggesting restitution of epithelial integrity compared to irradiated untreated control (*p<0.004, n=3 per group, unpaired t-test, two-tailed). Un-irradiated control mice and unirradiated BCN057 treated mice also showed lower serum dextran level compared to Irradiated control (*p<0.006 & *p<0.005, unpaired t-test, two-tailed).

Figure 7:
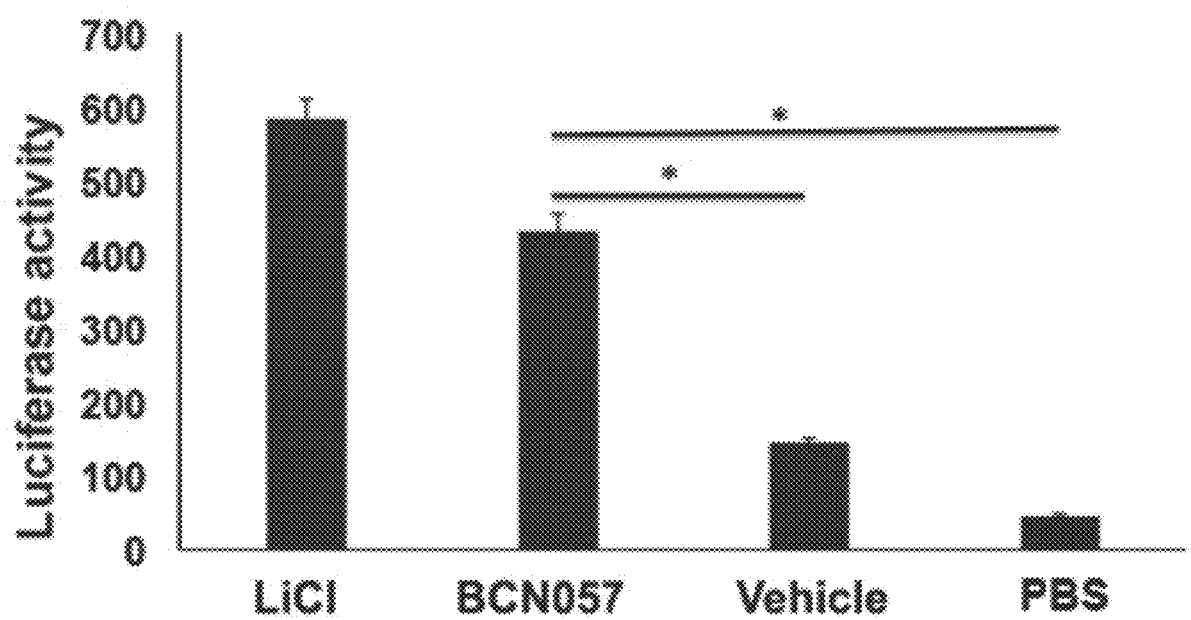
Figure 8:
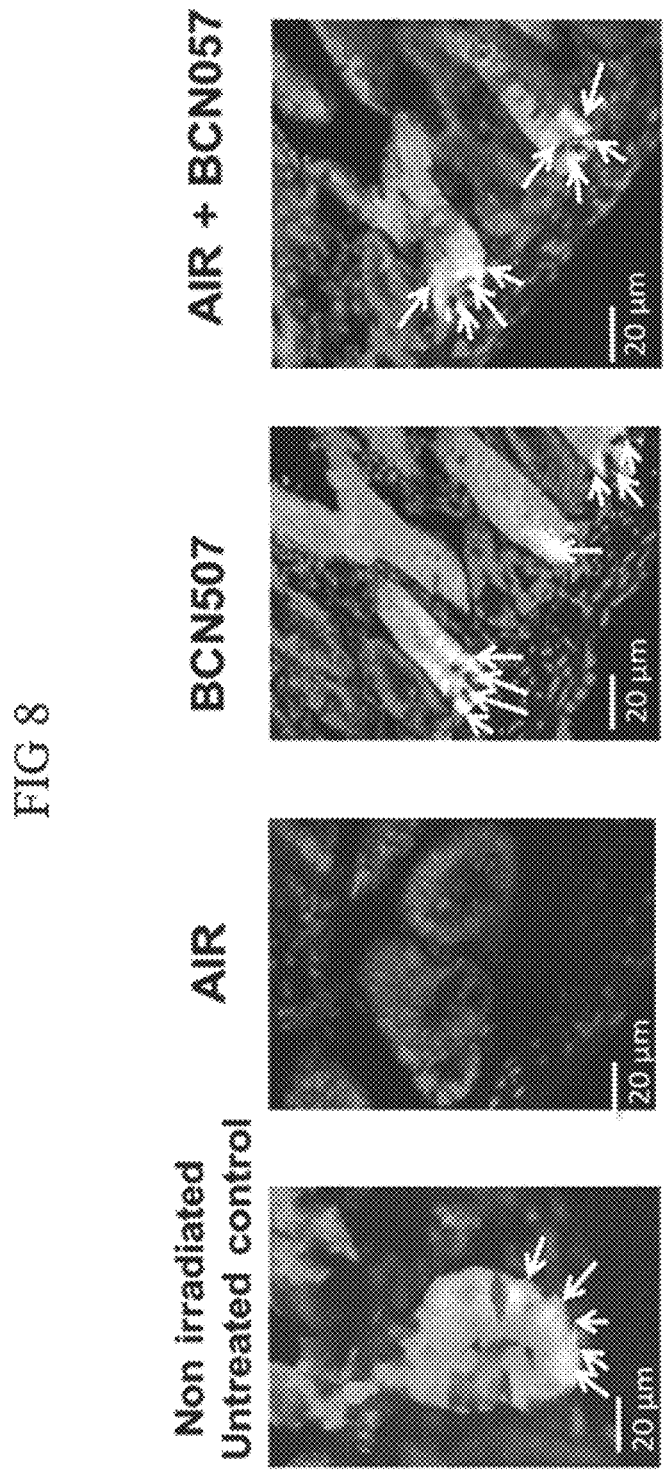
Figure 9:
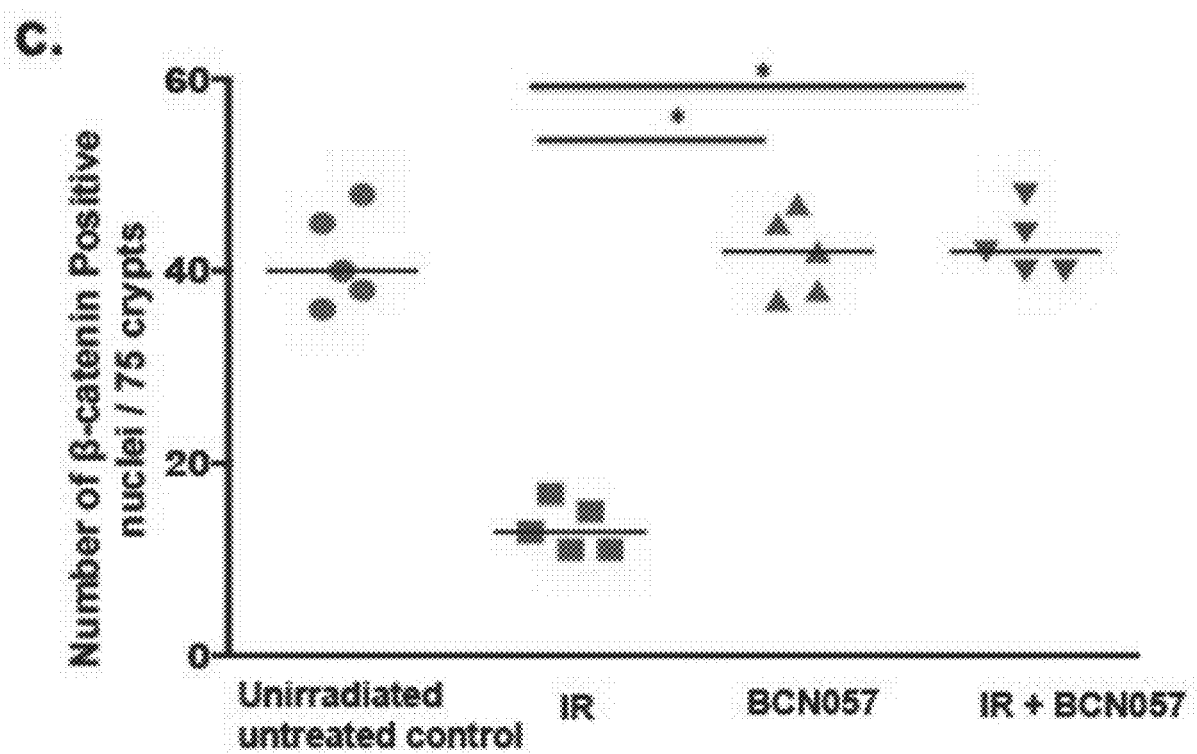

FIGS. 7-9: TCF/LEF reporter assay

FIG. 7. HEK293 cells having TCF/LEF luciferase reporter construct were treated with BCN057 or LiCl. Treatment with BCN057 showed higher Luciferase activity compared with vehicle control.

FIG. 8. Representative microscopic images (×60 magnification) of jejunal sections immunostained with anti β-catenin antibody to determine β-catenin nuclear localization. Nucleus stained with haematoxylin. Irradiated mice treated with BCN057 demonstrated more nuclear β-catenin staining (dark brown; indicated with arrows) at the base of the crypt compared to control nucleus stained blue.

FIG. 9 illustrates the effect of BCN057 analyzed in crypt epithelial β-catenin activation. Immuno-histochemical analysis of jejunal sections from non-irradiated mice showed characteristic β-catenin with 40+5 cells being positive for nuclear β-catenin per 75 crypts.

FIGS. 10, 11, 12A, and 12B: BCN057 rescued Lgr5+ISCs in both in vivo and in vitro FIG. 10. Microscopic image of intestinal organoids along with histogram demonstrating that BCN057 treatment improved the organoid growth compared to irradiated control.

Figure 11:
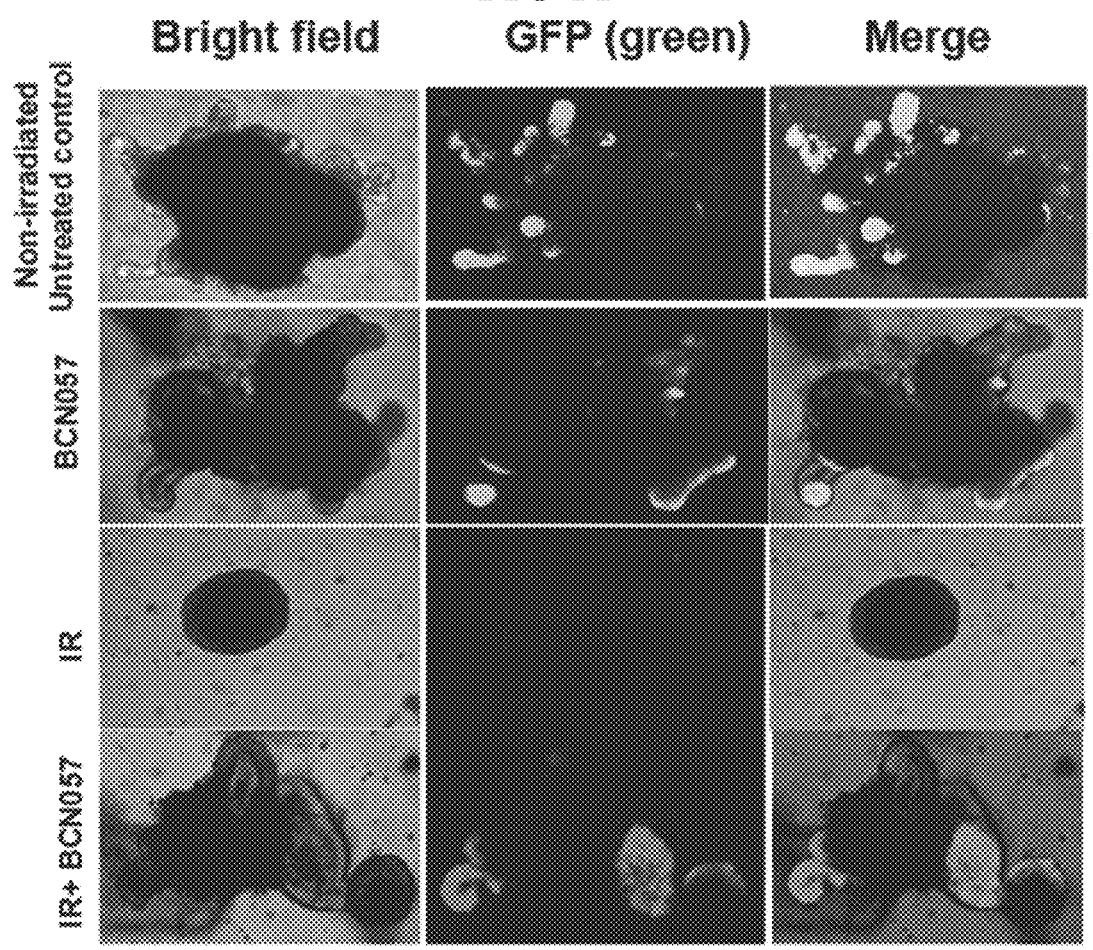

FIG. 11. Confocal microscopic images of organoids developed from Lgr5-EGFP-CRE-ERT2 mice demonstrated that BCN057 treatment increases the presence of Lgr5+ve cells in budding crypt compared irradiated control.

Figure 12A:
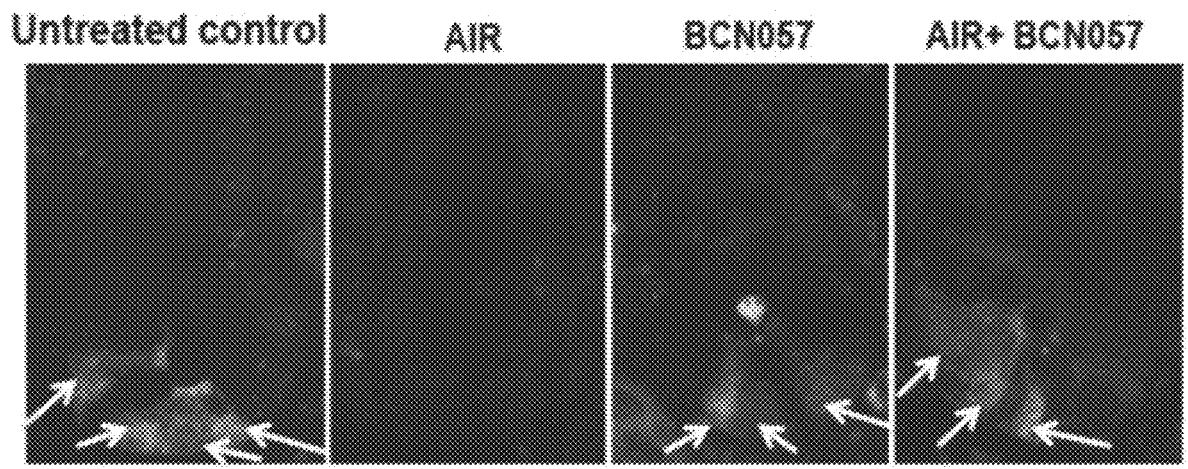

FIG. 12A. Representative images of jejunal sections demonstrating the presence of GFP+ve Lgr5+ve ISCs (arrow) in Lgr5/GFP-IRES-Cre-ERT2 knock-in mice receiving BCN057 24 hrs post AIR. Note, the absence of GFP+ve cells in mice receiving only AIR.

Figure 12B:
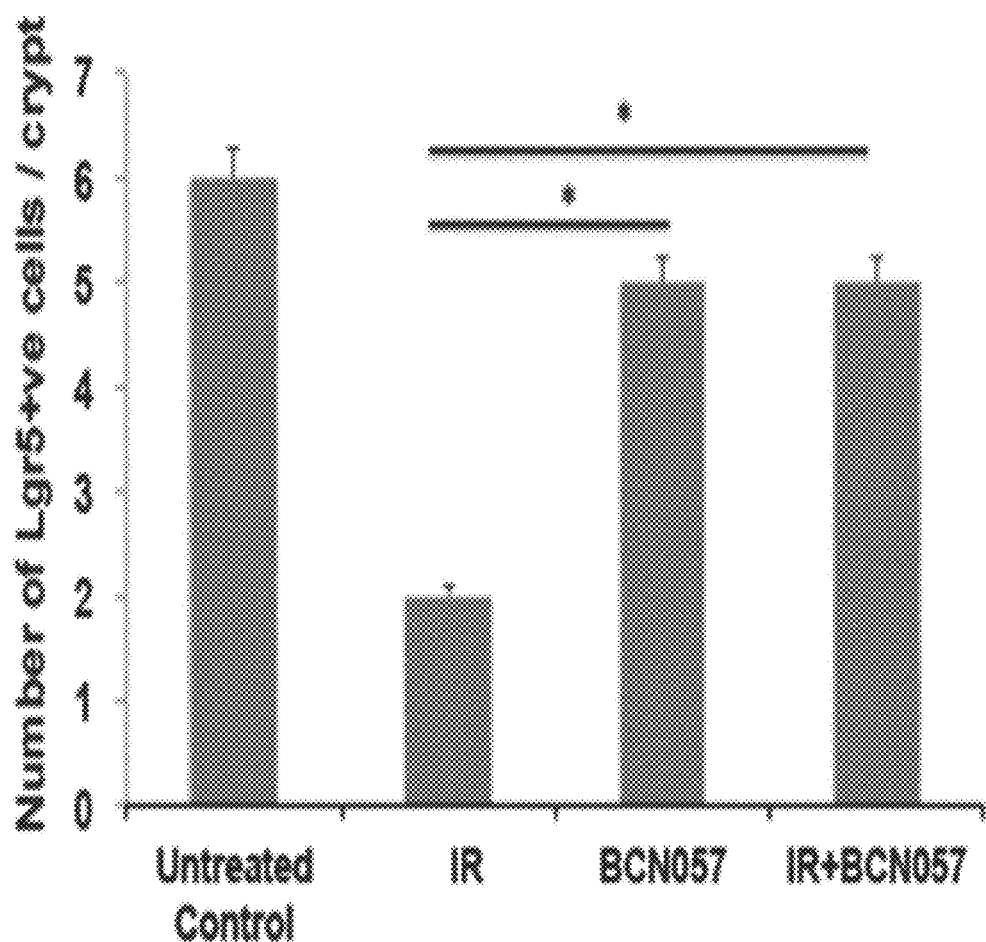

FIG. 12B. Histograms demonstrating the number of GFP+veLgr5+ve ISCs/crypt in jejunal sections from Lgr5/GFP-IRES-Cre-ERT2 knock-in mice exposed to irradiation and then treated with BCN057.

Figure 13:
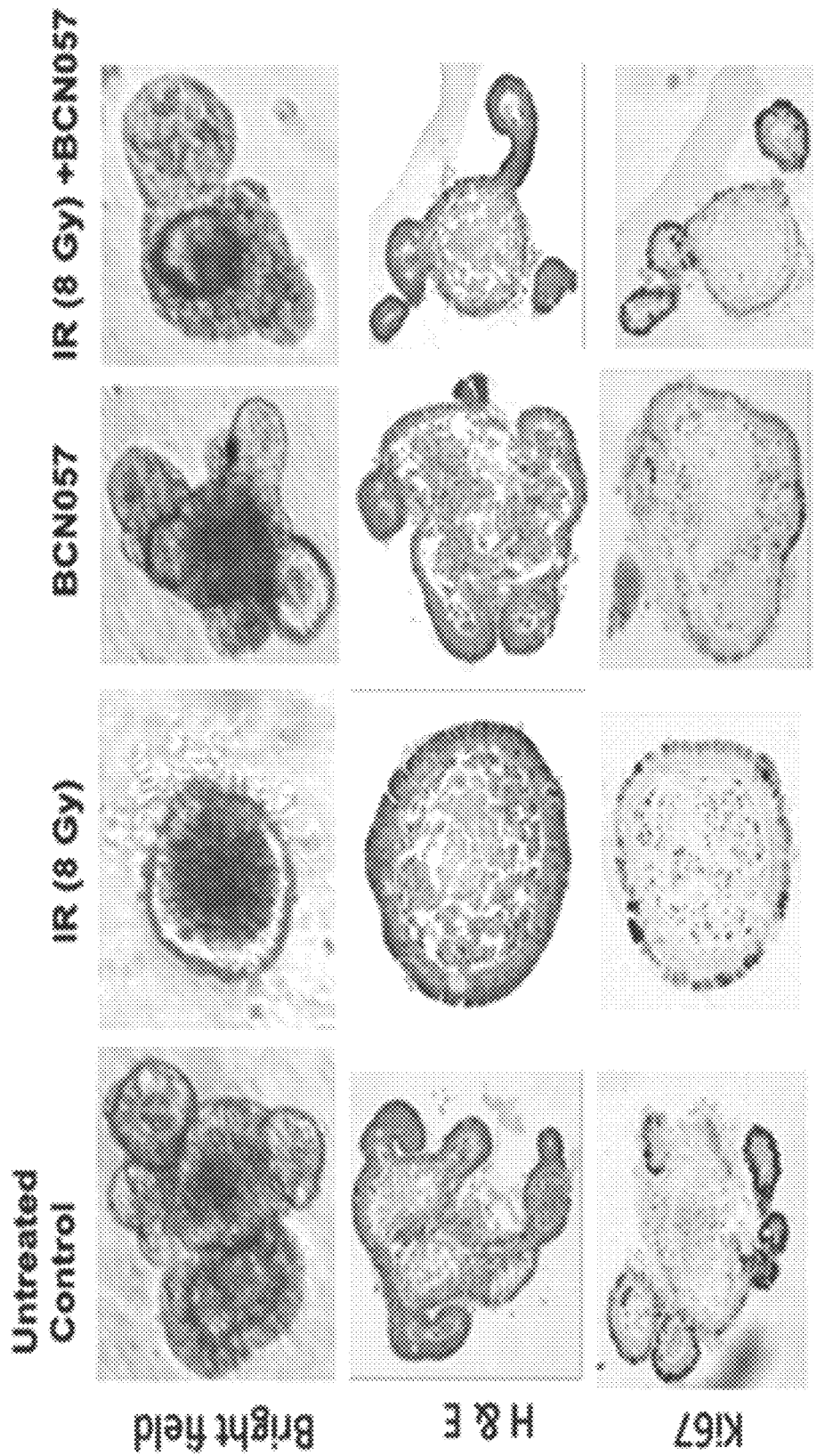
Figure 14:
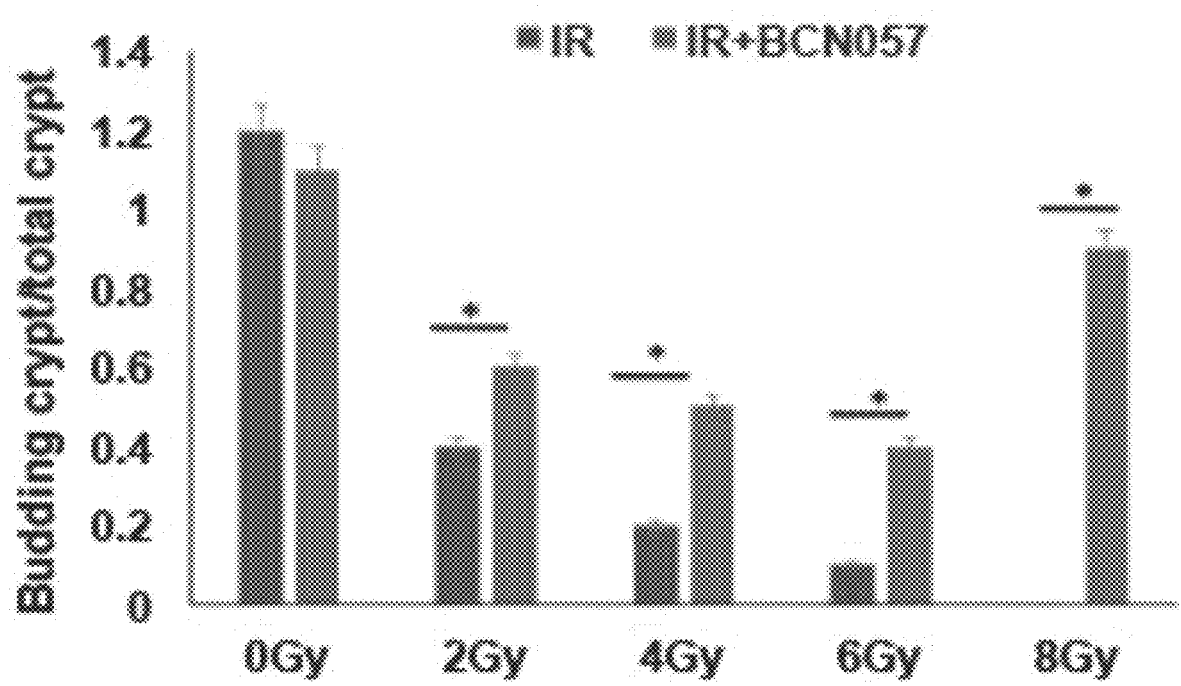
Figure 15:
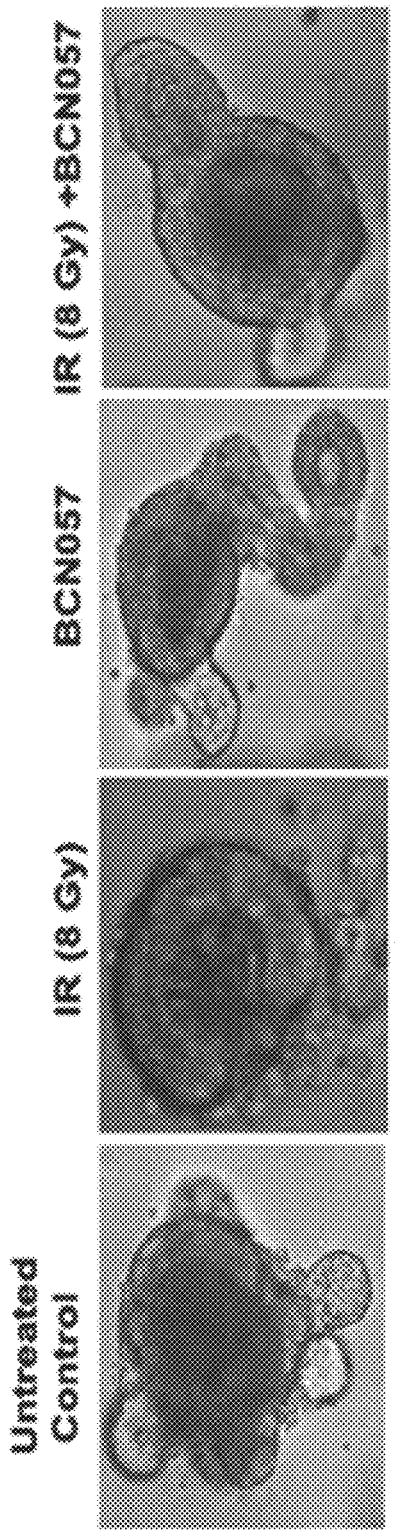

FIG. 13-15: BCN057 mitigates radiation toxicity in human colonic organoid developed from non-malignant tissue FIG. 13. Microscopic image demonstrating the loss of crypt domain in organoids exposed to irradiation (8Gy). Both bright field (top panel) and HE staining demonstrated complete loss of budding crypt at 72 hrs post irradiation. However, BCN057 treatment (20 ug/ml) at 1 hr post radiation rescued the organoids from radiation toxicity and accelerated crypt-villus budding. Note presence of budding crypt like structure in BCN057 treated group. Ki67 staining (lower panel) demonstrated positive staining in budding crypt like structure in BCN057 treated organoids indicating cell proliferation in this group. However, irradiated untreated organoids did not show any Ki67 positive budding crypt like structure.

FIG. 14. Ratio of budding crypt to total number of crypts are increased with BCN057 treatment in irradiated organoids compared to untreated irradiated control (4Gy *, p<0.006, 8Gy *, p<0.003) (Unpaired t test, two tailed).

FIG. 15. qPCR analysis demonstrated that BCN057 treatment increases the mRNA level of WNT target genes in epithelial cells isolated from irradiated human colonic organoids. (B-C, Data was the average of 3 human subjects).

Figure 16:
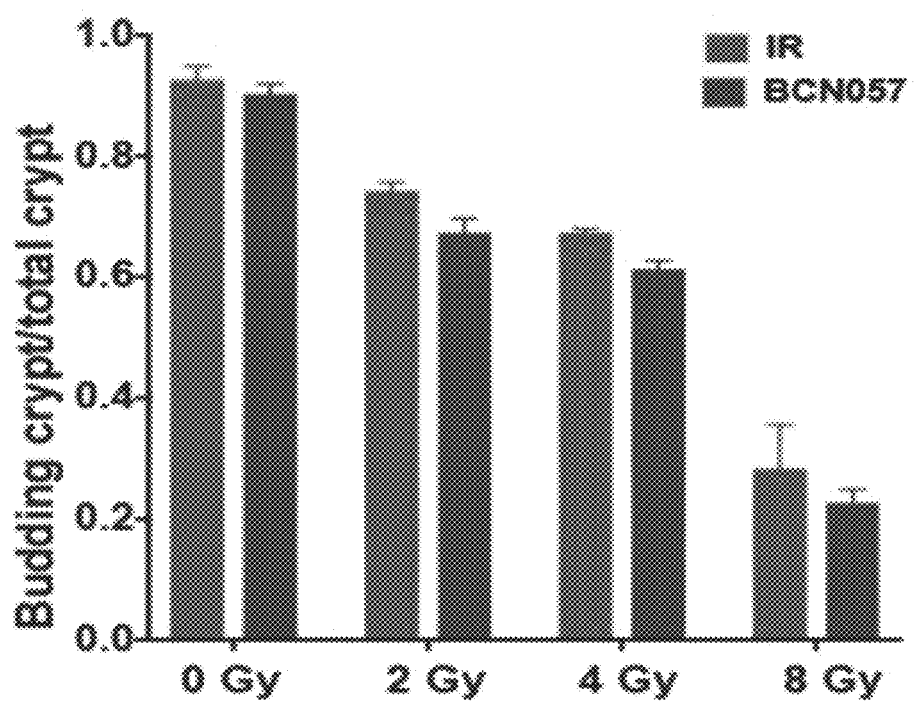
Figure 17:
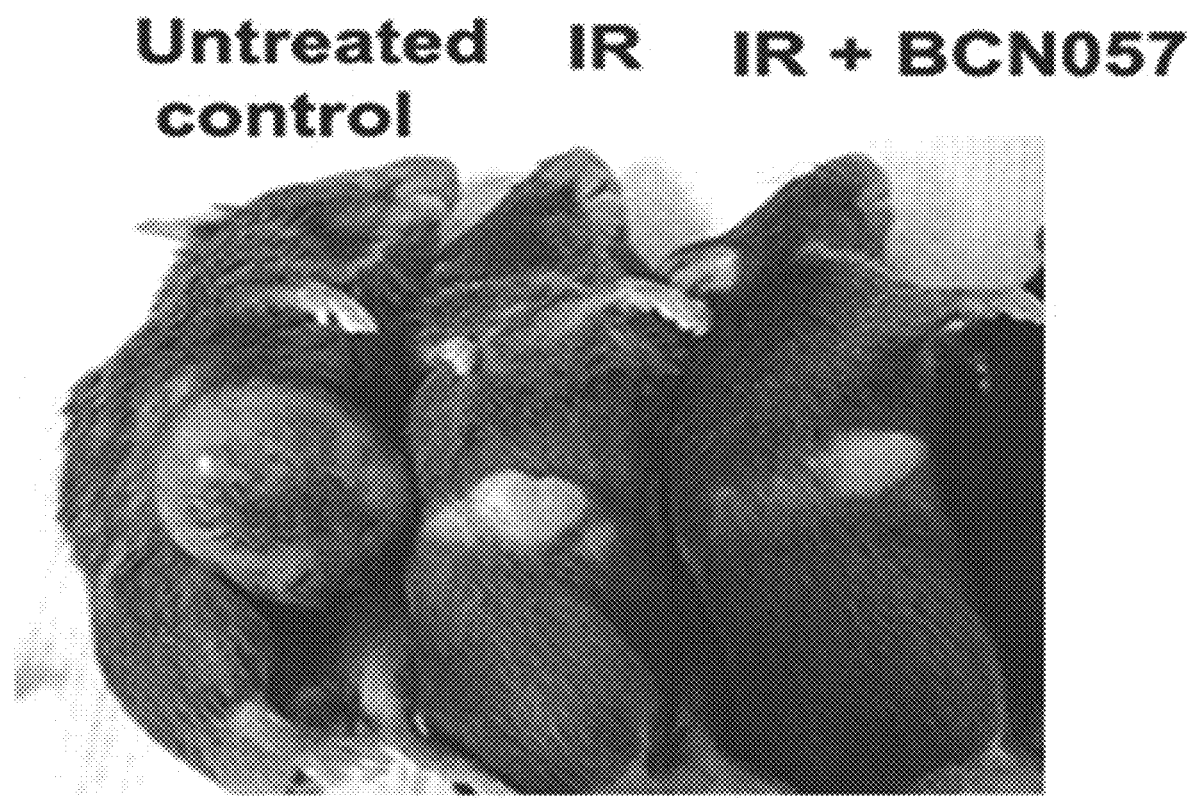
Figure 18:
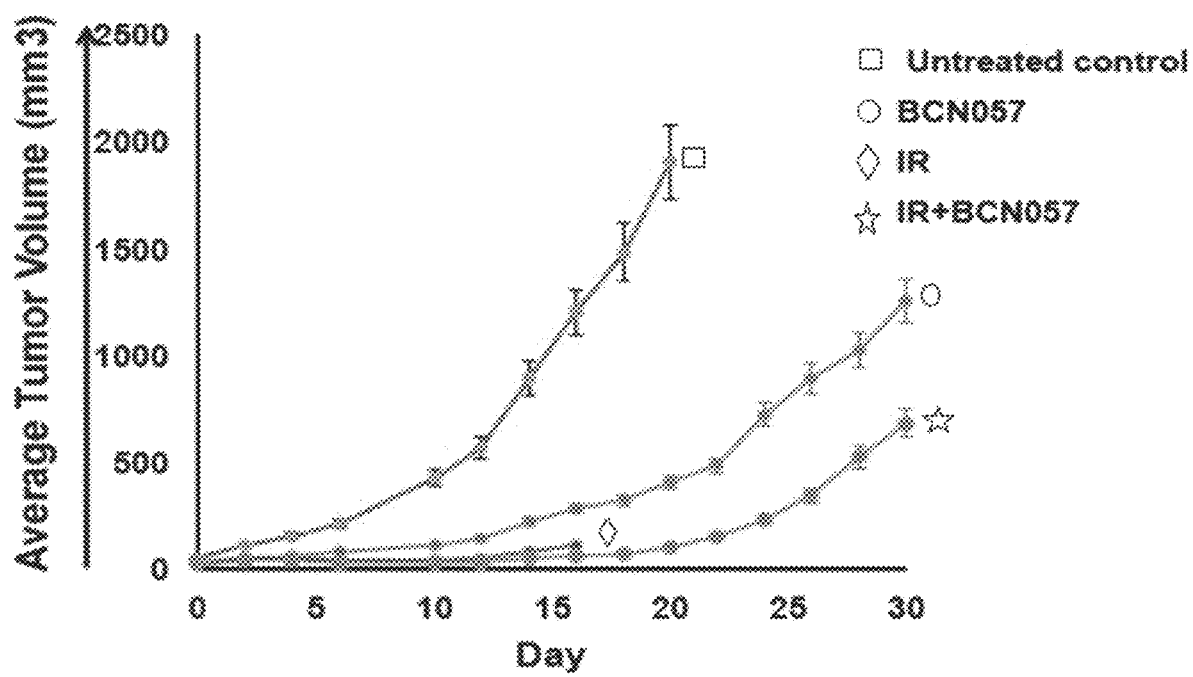

FIGS. 16-18: BCN057 does not have any radio-protective effect on colonic tumor tissue FIG. 16. BCN057 treatment did not rescue human malignant colonic organoids from radiation toxicity. Organoids derived from surgical specimen of colon tumor were exposed to irradiation (8Gy) and then treated with BCN057. Note loss of budding crypt like structure in Irradiated organoids treated with BCN057. Treatment with BCN057 in un-irradiated organoids also showed the loss of budding crypt like structure indicating that BCN057 has an inhibitory effect on the growth and proliferation of malignant organoid.

FIG. 17. Histogram demonstrating effect of BCN057 treatment on the growth of irradiated crypt organoids developed from human colon tumor. Budding crypt to total crypt ratio reduced in a dose dependent manner following irradiation (2-8 Gy). Similar pattern of Budding crypt to total crypt ratio was observed in irradiated organoids with BCN057 treatment indicating that BCN057 could not reduce the radiation toxicity in malignant colonic organoids.

FIG. 18. BCN057 does not have radio-protective effect on mice abdominal tumor. I) Schematic diagram of BCN057 treatment in C57B16 mice having MC38 colon tumor in the flank. Mice were exposed to AIR (15Gy) and then treated with BCN057 at 24 hrs post exposure. Ii) Representative image of C57B16 mice having MC38 colon tumor in the flank. Note reduction in tumor size in irradiated or un-irradiated tumor treated with BCN057 at day 20 post AIR. Mice exposed to AIR without BCN057 treatment are not part of this image as they died within day 15 post AIR. Iii) Tumor growth curve demonstrating the effect of BCN057 treatment on mice abdominal MC38 tumor. Note significant reduction of tumor growth in BCN057 treated mice following AIR compared to un-irradiated untreated control. BCN057 treatment in un-irradiated mice also reduces the tumor growth compared to un-irradiated untreated control.

Figure 19:

FIG. 19: Oral Mucositis

FIG. 19 shows tongue size 9 days post-head and neck irradiation (30Gy) in mice.

Figure 20:
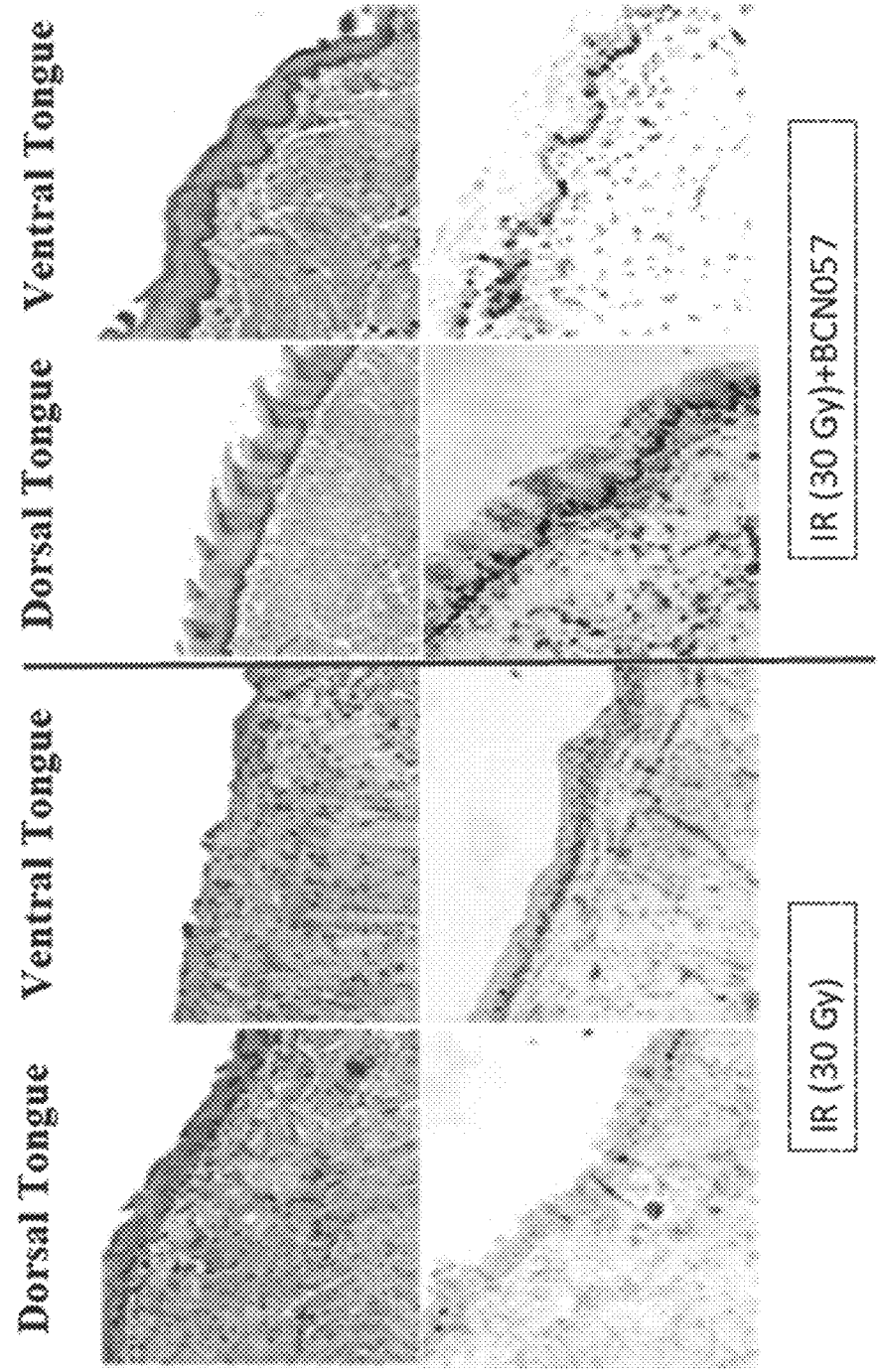

FIG. 20: Oral Mucositis

FIG. 20 shows histopathological analysis in mucosal thickness with BCN057 treatment following head and neck irradiation (30Gy).

DETAILED DESCRIPTION OF THE DISCLOSURE

Radiation Induced Gastro Intestinal Syndrome (RIGS) limits the survival of victims in a mass casualty setting from nuclear accidents or terrorism. Currently there is no approved therapy for protecting or mitigating RIGS resulting from direct cytocidal effects on intestinal stem cells. The present disclosure demonstrates that BCN057, an anti-neoplastic small molecular agent, activates Wnt-β catenin signaling a key-signaling pathway for intestinal epithelial homeostasis and regeneration. Treatment with BCN057 after lethal dose of 15Gy abdominal irradiation mitigated RIGS and improved survival of mice compared to irradiated control where all the mice were dead within 10 to 15 days post-irradiation. Mice that received BCN057 continued to survive for months after AIR without any sign/symptom of RIGS or radiation enteritis. BCN057 rescued intestinal stem cells from radiation toxicity and improved the survival of irradiated crypt organoids developed from mice jejunum or human colon. However, BCN057 did not deliver any radio-protection to mouse or human colon tumor tissue. Therefore, BCN057 is an agent for mitigation of RIGS as well as improvement of therapeutic ratio for abdominal radiotherapy.

Furthermore, BCN057 mitigates radiation induced mucositis, including oral mucositis, GI mucositis, e.g., of the throat, stomach and intestines, enteritis and proctitis. It is also useful for treating or preventing these radiation syndromes associated with radiation therapy. Analogs of BCN057 are also useful in the methods of the disclosure.

Mucositis or GI mucositis is a common side effect of chemotherapy and of radiotherapy that involves any part of the digestive tract, is the painful inflammation and ulceration of the mucous membranes lining the digestive tract. Mucositis affects the rapidly dividing mucosal cells that line the mouth (oral mucositis), throat, stomach, and small and large intestines (enteritis), which normally have a short lifespan. Proctitis is a mucositis of the rectum Radiation enteritis is a malfunction of the large and small bowel that occurs during or after radiation therapy to the abdomen, sexual organs, pelvis, or rectum, including treatment for cervical, pancreatic, prostate, uterine, colon and rectal cancer. Proctitis is a related radiation induced inflammation of the rectum.

Severity varies, with approximately 15-20% of patients requiring an altered therapeutic course. It is usually self-limiting, often resolves within 3 months and frequently only requires supportive measures (Do et al. (2011) Gastroenterol Res Practice 2011: 917941). Chronic small bowel radiation disease typically develops between 18 months and 6 years after a completed course of radiotherapy, but has been reported to present up to 30 years later (Kountouras and Zavos (2008) World J Gastroenterol 14: 7289-7301). It is a more common entity than many doctors think: 90% of patients who receive pelvic radiotherapy develop a permanent change in their bowel habit (Olopade et al. (2005) Br J Cancer 92: 1663-1670). It is also problematic, 50% of patients with pelvic irradiation describe their quality of life has been adversely affected by a variety of GI symptoms with 20-40% (depending on tumor type) rating the effect on quality of life as moderate or severe (Widmark et al., (1994) Cancer 74: 2520-2532; Crook, et al., (1996) URL 47: 387-394; Gami, et al. (2003) Aliment Pharmacol Therapeut 18(10), pp. 987-994; and Andreyev (2007 Clin Oncol 19: 790-799).

Oral mucositis is probably the most common, debilitating complication of cancer treatments, particularly chemotherapy and radiation. It can lead to a number of problems, including pain, nutritional problems as a result of inability to eat, and increased risk of infection due to open sores in the mucosa. It has a significant effect on the patient's quality of life and can be dose-limiting (i.e., requiring a reduction in subsequent chemotherapy doses).

In one aspect, disclosed herein is a method of treating the subject with a therapeutically effective amount of a compound of Formula I:

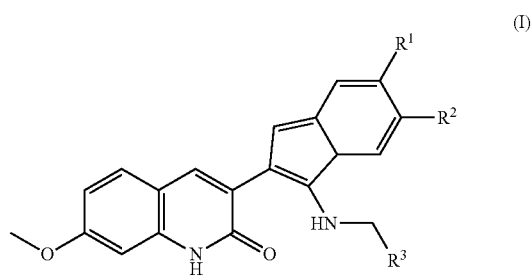

(I)

$R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl.

The structure of compound YEL002/BCN057 is shown below as Formula IA:

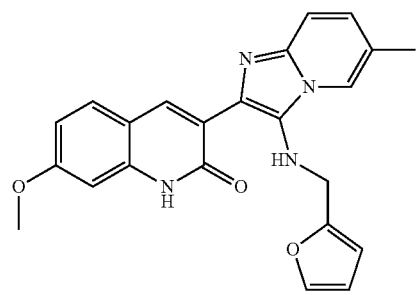 [SMILES: COc1ccc2cc(-c3nc4ccc(C)cn4c3NCc3ccco3)c(=O)[nH]c2c1]

Yel002 or BCN057 is also known as 3-(3((furan-2-ylmethyl)ammo)-6-methylimidazo[1,2-a]pyridine-2-yl)-6-methoxyquinolin-2(1H)-one.

In some embodiments, the compound is an analog of Formula IA selected from Formulae IB-II:

Formula IB
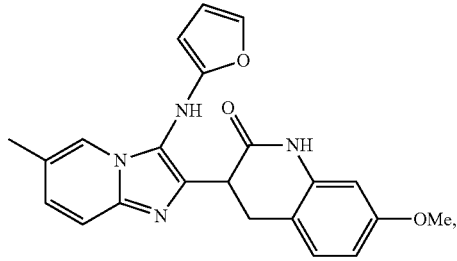

Formula IC
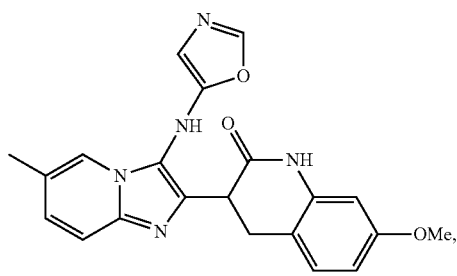

Formula ID
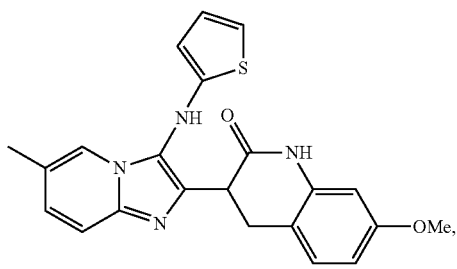

Formula IE
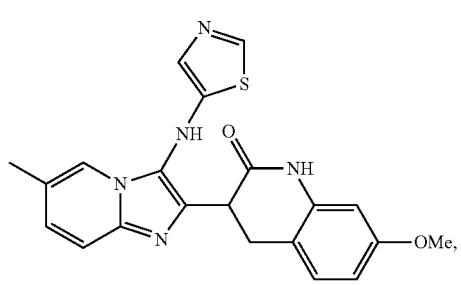

Formula IF
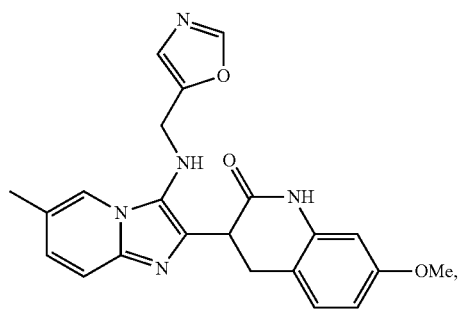

Formula IG
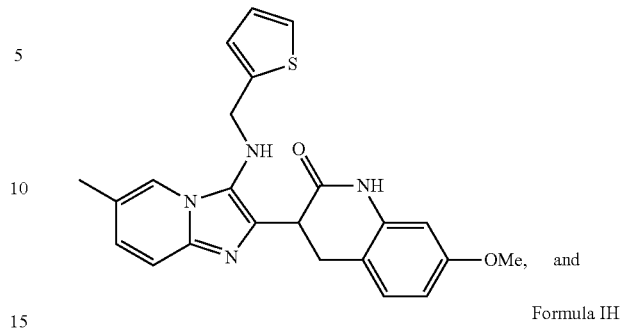

and

Formula IH
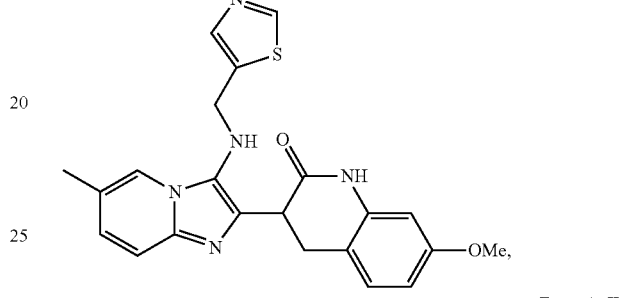

Formula II
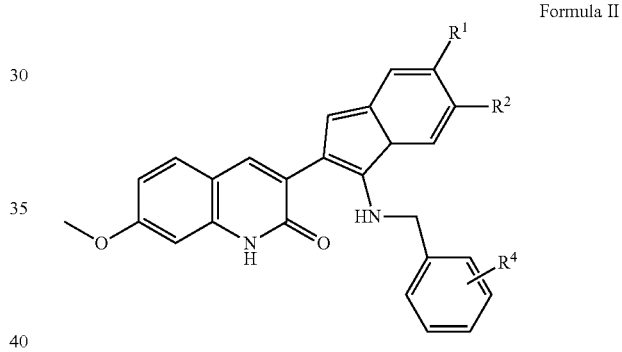

Wherein $R^4$ is an optional substituent as disclosed herein.

The term "alkoxy" represents a chemical substituent of formula —OR, where R is an optionally substituted $C_1$-$C_6$ alkyl group, unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

The terms "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. Typically, the alkyl, alkenyl and alkynyl groups contain 1-12 carbons (e.g., $C_1$-$C_{12}$ alkyl) or 2-12 carbons (e.g., $C_2$-$C_{12}$ alkenyl or $C_2$-$C_{12}$ alkynyl). In some embodiments, the alkyl groups are $C_1$-$C_8$, $C_1$-$C_3$, or $C_1$-$C_2$ alkyl groups; or $C_2$-$C_8$, $C_2$-$C_6$, $C_2$-$C_4$, or $C_2$-$C_3$ alkenyl or alkynyl groups. Further, any hydrogen atom on one of these groups can be replaced with a substituent as described herein.

Heteroalkyl, heteroalkenyl and heteroalkynyl are similarly defined and contain at least one carbon atom but also contain one or more 0, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In some embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In some embodiments, the heteroatom is O or N. The term "heterocyclyl," as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopenlane ring, a cyclopentene ring, or another monocyclic heterocyclic ring, such as indolyl, quinolyl, isoquinolyl, tetrahydroquinolyl, benzofuryl, benzothienyl and the like.

The term "alkylsulfonyl," as used herein, represents a heteroalkyl group that is described as an optionally substituted alkyl group, as described herein, that includes an —S(O)$_2$— group.

The term "amino," as used herein, represents —N(R)$_2$, wherein each R is, independently, H, OH, NO$_2$, N(R)$_2$, SO$_2$OR, SO$_2$R, SOR, SO$_2$N(R)$_2$, SON(R)$_2$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two R combine to form a heterocyclyl or an N-protecting group, and wherein each R' is, independently, H, alkyl, or aryl. In a preferred embodiment, amino is —NH$_2$, or —NHR, wherein R is, independently, OH, NO$_2$, NH$_2$, NR$_2$, SO$_2$OR, SO$_2$R, SOR, SO$_2$N(R)$_2$, SON(R)$_2$, alkyl, or aryl, and each R can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (=O) substituent.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl or benzimidazolyl, pyrazolyl, imidazolyl, isoxazolyl, thiazolyl, benzothiazolyl, indolyl. Even more particularly, such moiety is phenyl, pyridyl, or pyrimidyl and even more particularly, it is phenyl. "O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of $C_1$-$C_2$, $C_1$-$C_6$, or more particularly $C_1$-$C_4$ or $C_1$-$C_3$ when saturated or $C_2$-$C_8$, $C_2$-$C_6$, $C_2$-$C_4$, or $C_2$-$C_3$ when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl($C_6$-$C_{12}$)alkyl($C_1$-$C_8$), aryl($C_6$-$C_{12}$)alkenyl ($C_2$-$C_8$), or aryl($C_6$-$C_{12}$)alkynyl($C_2$-$C_8$), plus the heteroforms. A typical example is phenylmethyl, commonly referred to as benzyl.

Halo may be any halogen atom, especially F, Cl, Br, or I, and more particularly it is fluoro or chloro.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls. In some embodiments, the haloalkyl group can be further substituted with 1, 2, 3, or 4 substituent groups as described herein for alkyl groups.

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. For example, where a group is substituted, the group may be substituted with 1, 2, 3, 4, 5, or 6 substituents. Optional substituents include, but are not limited to: $C_1$-$C_6$ alkyl or heteroaryl, $C_2$-$C_6$ alkenyl or heteroalkenyl, $C_2$-$C_6$ alkynyl or heteroalkynyl, halogen; aryl, heteroaryl, azido(—$N_3$), nitro (—$NO_2$), cyano (—CN), acyloxy (—OC(=O)R'), acyl (—C(=O)R'), alkoxy (—OR'), amido (—NR'C(=O)R" or —C(=O)NR'R"), amino (—NR'R"), carboxylic acid (—$CO_2H$), carboxylic ester (—$CO_2R'$), carbamoyl (—OC(=O)NR'R" or —NRC(=O)OR), hydroxy (—OH), isocyano (—NC), sulfonate (—S(=OHOR), sulfonamide (—S(=OHNRR' or —NRS(=O)$_2$R), or sulfonyl (—S(=O)$_2$R), where each R or R' is selected, independently, from H, $C_1$-$C_6$ alkyl or heteroaryl, $C_2$-$C_6$ alkenyl or heteroalkenyl, $C_2$-$C_6$ alkynyl or heteroalkynyl, aryl, or heteroaryl. A substituted group may have, for example, 1, 2, 3, 4, 5, 6, 7, 8, or 9 substituents.

Typical optional substituents include independently halo, CN, $NO_2$, $CF_3$, $OCF_3$, COOR, $CONR^Y_2$, OR, SR, SOR, $SO_2R$, $NR_2$, NR(CO)R, NRC(O)OR, NRC(O)$NR_2$, $NRSO_2NR_2$, or $NRSO_2R$, wherein each R is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

A compound of Formula IA, or an analog thereof disclosed herein can be prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Exemplary methods of making the compound is provided in U.S. Ser. No. 13/813,923 and U.S. Ser. No. 14/889,719, herein incorporated by reference in their entirety. The compound also includes a pharmaceutically acceptable salt thereof, a prodrug thereof, a hydrate thereof, a solvate thereof, or a polymorphic crystal thereof. The compound may be administered as a pharmaceutical composition.

The present methods may prevent a disease or condition or one or more symptoms of a disease or condition. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The compositions and methods of the present disclosure may be utilized to treat an individual in need thereof. In certain embodiments, the individual is a mammal such as a human, or a non-human mammal. When administered to an animal, such as a human, the composition or the compound is preferably administered or used as a pharmaceutical composition comprising, for example, a compound of the disclosure and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophilized for reconstitution, powder, solution, syrup, suppository, injection or the like. The composition can also be present in a transdermal delivery system, e.g., a skin patch.

A pharmaceutical composition disclosed herein may comprise a therapeutic compound in an amount sufficient to allow customary administration to an individual. In certain embodiments, a pharmaceutical composition disclosed herein may comprise, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In certain embodiments, a pharmaceutical composition disclosed herein may comprise, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may comprise in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still certain embodiments, a pharmaceutical composition disclosed herein may comprise in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a therapeutic compound disclosed herein. In certain embodiments, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In certain embodiments, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic compound disclosed herein in a pharmaceutical composition disclosed herein may be of any suitable concentration. In certain embodiments, the final concentration of a therapeutic compound in a pharmaceutical composition may be a therapeutically effective amount. In certain embodiments, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In certain embodiments, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In certain embodiments, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

In certain embodiments, a therapeutically effective amount of a therapeutic compound disclosed herein generally is in the range of about 0.001 mg/kg/day to about 100 mg/kg/day. In certain embodiments, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In certain embodiments, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, about 0.001 mg/kg/day to about 100 mg/kg/day, about 0.001 mg/kg/day to about 150 mg/kg/day, about 0.001 mg/kg/day to about 200 mg/kg/day, about 0.001 mg/kg/day to about 250 mg/kg/day, about 0.001 mg/kg/day to about 300 mg/kg/day, about 0.001 mg/kg/day to about 350 mg/kg/day, about 0.001 mg/kg/day to about 400 mg/kg/day, about 0.001 mg/kg/day to about 450 mg/kg/day, about 0.001 mg/kg/day to about 500 mg/kg/day, about 0.001 mg/kg/day to about 550 mg/kg/day, about 0.001 mg/kg/day to about 600 mg/kg/day, about 0.001 mg/kg/day to about 650 mg/kg/day, about 0.001 mg/kg/day to about 700 mg/kg/day, about 0.001 mg/kg/day to about 750 mg/kg/day, or about 0.001 mg/kg/day to about 800 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, about 0.01 mg/kg/day to about 100 mg/kg/day, about 0.01 mg/kg/day to about 150 mg/kg/day, about 0.01 mg/kg/day to about 200 mg/kg/day, about 0.01 mg/kg/day to about 250 mg/kg/day, about 0.01 mg/kg/day to about 300 mg/kg/day, about 0.01 mg/kg/day to about 350 mg/kg/day, about 0.01 mg/kg/day to about 400 mg/kg/day, about 0.01 mg/kg/day to about 450 mg/kg/day, about 0.01 mg/kg/day to about 500 mg/kg/day, about 0.01 mg/kg/day to about 550 mg/kg/day, about 0.01 mg/kg/day to about 600 mg/kg/day, about 0.01 mg/kg/day to about 650 mg/kg/day, about 0.01 mg/kg/day to about 700 mg/kg/day, about 0.01 mg/kg/day to about 750 mg/kg/day, or about 0.01 mg/kg/day to about 800 mg/kg/day. In certain embodiments, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, about 0.1 mg/kg/day to about 100 mg/kg/day, about 0.1 mg/kg/day to about 150 mg/kg/day, about 0.1 mg/kg/day to about 200 mg/kg/day, about 0.1 mg/kg/day to about 250 mg/kg/day, about 0.1 mg/kg/day to about 300 mg/kg/day, about 0.1 mg/kg/day to about 350 mg/kg/day, about 0.1 mg/kg/day to about 400 mg/kg/day, about 0.1 mg/kg/day to about 450 mg/kg/day, about 0.1 mg/kg/day to about 500 mg/kg/day, about 0.1 mg/kg/day to about 550 mg/kg/day, about 0.1 mg/kg/day to about 600 mg/kg/day, about 0.1 mg/kg/day to about 650 mg/kg/day, about 0.1 mg/kg/day to about 700 mg/kg/day, about 0.1 mg/kg/day to about 750 mg/kg/day, or about 0.1 mg/kg/day to about 800 mg/kg/day. In certain embodiments, an effective amount of a therapeutic compound disclosed herein may be in the range of, e.g., about 10 mg/kg/day to about 15 mg/kg/day, about 10 mg/kg/day to about 20 mg/kg/day, about 10 mg/kg/day to about 25 mg/kg/day, about 10 mg/kg/day to about 30 mg/kg/day, about 10 mg/kg/day to about 35 mg/kg/day, about 10 mg/kg/day to about 40 mg/kg/day, about 10 mg/kg/day to about 45 mg/kg/day, about 10 mg/kg/day to about 50 mg/kg/day, about 10 mg/kg/day to about 75 mg/kg/day, about 10 mg/kg/day to about 100 mg/kg/day, about 10 mg/kg/day to about 150 mg/kg/day, about 10 mg/kg/day to about 200 mg/kg/day, about 10 mg/kg/day to about 250 mg/kg/day, about 10 mg/kg/day to about 300 mg/kg/day, about 10 mg/kg/day to about 350 mg/kg/day, about 10 mg/kg/day to about 400 mg/kg/day, about 10 mg/kg/day to about 450 mg/kg/day, about 10 mg/kg/day to about 500 mg/kg/day, about 10 mg/kg/day to about 550 mg/kg/day, about 10 mg/kg/day to about 600 mg/kg/day, about 10 mg/kg/day to about 650 mg/kg/day, about 10 mg/kg/day to about 700 mg/kg/day, about 10 mg/kg/day to about 750 mg/kg/day, or about 10 mg/kg/day to about 800 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In certain embodiments, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of a therapeutic compound disclosed herein typically may be between about 50 mg/mL to about 1,000 mg/mL. In certain embodiments, a therapeutically effective amount of a therapeutic disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

As used herein, "mitigating" means reducing one or more negative symptoms of a condition, relative to a cell, organ, tissue, or organism displaying the symptom or condition for the same amount of time, but untreated.

In some embodiments, contacting the cell, organ, tissue, or organism the present compounds may comprise administering a therapeutically effective amount of the compound to a subject. As used herein, a "therapeutically effective amount" is an amount sufficient to mitigate the negative symptom or condition.

The subject may be a human, rat, mouse, cat, dog, horse, sheep, cow, monkey, avian, or amphibian. In another embodiment, the cell is in vivo or in vitro. Typical subjects to which compounds of the disclosure may be administered will be mammals, particularly primates, especially humans. For veterinary applications, a wide variety of subjects will be suitable, e. g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

When administering to an organism, the compound may be administered by any suitable means. In some embodiments, the compounds or formulations are administered orally. In some embodiments, the compounds or formulations are administered by injection, e.g. subcutaneous, parenteral, or intravenous, injections.

In some embodiments the compound may be administered in combination with other potential mitigators. In a particular embodiment, the composition may be administered with growth factors, NSAIDs, chemotherapeutics, anti-inflammatories, antibiotics, Metformin (Glucophage, Glumetza, others), Sulfonylureas, Meglitinides, Thiazolidinediones, DPP-4 inhibitors, GLP-1 receptor agonists, SGLT2 inhibitors, and/or Insulin therapy, for the treatment of the above conditions. In one aspect, the growth factor can be G-CSF (aka filgrastim, NEUPOGEN®) or erythropoietin (aka EPOGEN®).

In other embodiments, the compositions may comprise an effective amount of a modulator and/or other pharmaceutically active agent in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin. In some embodiments, the compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In some embodiments, the compositions may be in a form suitable for administration by sterile injection. In one example, to prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed. In one embodiment, the formulation includes at least one or more of methanesulfonic acid, povidone, benzyl alcohol, n-Methyl pyrrolidone, ethaonol, Poloxamer 188, lactic acid, Captisol (SBE-beta-CD), or Vitamin E, such as TPGS (d-alpha tocopheryl polyethylene glycol 1000 succinate).

Formulations suitable for parenteral administration usually comprise a sterile aqueous preparation of the compound, which may be isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In some embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition may be in a form of nasal or other mucosal spray formulations (e.g. inhalable forms). These formulations can include purified aqueous solutions of the active compounds with preservative agents and isotonic agents. Such formulations can be adjusted to a pH and isotonic state compatible with the nasal or other mucous membranes. Alternatively, they can be in the form of finely divided solid powders suspended in a gas carrier.

Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared, for example, by incorporating the active compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the disclosure may further include one or more accessory ingredient(s) selected from encapsulants, diluents, buffers, flavoring agents, binders, disintegrants, surface active agents, thickeners, lubricants, preservatives (including antioxidants), and the like.

In some embodiments, compositions may be formulated for immediate release, sustained release, delayed-onset release or any other release profile known to one skilled in the art. In some embodiments, the pharmaceutical composition may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the compound in a liposome or other encapsulate medium, or by fixation of the compound, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the compound may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

In all embodiments, the compound or other active compounds may be present as pharmaceutically acceptable salts or other derivatives, such as ether derivatives, ester derivatives, acid derivatives, and aqueous solubility altering derivatives of the active compound. Derivatives include all individual enantiomers, diastereomers, racemates, and other isomers of the compounds. Derivatives also include all polymorphs and solvates, such as hydrates and those formed with organic solvents, of the compounds. Such isomers, polymorphs, and solvates may be prepared by methods known in the art, such as by regiospecific and/or enantioselective synthesis and resolution.

The ability to prepare salts depends on the acidity or basicity of the compounds. Suitable salts of the compounds include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methyl sulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless the context clearly indicates otherwise, compositions of all embodiments can comprise various pharmaceutically acceptable salts, or other derivatives described above.

The formulation and preparation of such compositions are well known to those skilled in the art of pharmaceutical formulation. Formulations can be found in Remington: The Science and Practice of Pharmacy.

The amount of the compound employed in the present disclosure to be used varies according to the condition, the patient/subject, and the extent of the condition.

The contents of all cited references (including literature references, issued patents, published patent applications) as cited throughout this application are hereby expressly incorporated by reference. The disclosure and the manner and process of making and using it, are described in such full, clear, concise and exact terms as to enable any person skilled in the art to which it pertains, to make and use the same.

The term "unit dosage form" or "unit" as used herein refers to physically discrete units suitable as unitary dosages for human and animal subjects, each unit containing a predetermined quantity of the compound calculated in an amount sufficient to produce the desired effect in association with a pharmaceutically acceptable, diluent, carrier or vehicle. The specifications for the novel unit dosage forms of the present disclosure depend on the particular compound employed and the effect to be achieved, and the pharmacodynamics associated with each compound in the subject.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

Dosing can be single dosage or cumulative (serial dosing), and can be readily determined by one skilled in the art. For instance, treatment may comprise a one-time administration of an effective dose of a pharmaceutical composition disclosed herein. Alternatively, treatment may comprise multiple administrations of an effective dose of a pharmaceutical composition carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

In certain embodiments, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In certain embodiments, a treatment regimen may comprise a period during which administration is stopped for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

The patient receiving this treatment is any animal in need, including primates, in particular humans, and other mammals such as equines, cattle, swine and sheep; and poultry and pets in general.

In other embodiments, the compounds described herein may be provided with the one or more additional therapeutic agents in a kit, e.g., as separate pharmaceutical formulations capable of being used together in a conjoint therapy as discussed herein, either together in a single container or in separate containers. In certain such embodiments, the kit may further include instructions for the conjoint administration of the pharmaceutical formulations, e.g., for treating or preventing any of the conditions discussed above.

Such combination products may employ compounds of this disclosure, or pharmaceutically acceptable salts thereof, within the dosage range described hereinbefore and the other pharmaceutically-active agent within its approved dosage range.

In some embodiments, the compound may be administered after the predicate event, such as after exposure to ionizing radiation, or after the initiation of exposure to radiation including accidental or therapeutic radiation. In one embodiment, the compound is administered immediately after the exposure. In another embodiment, the compound is administered within 12 hours of the exposure. In another embodiment, the compound is administered within 24 hours of the exposure. In another embodiment, the compound is administered at 24 hours after the exposure. In another embodiment, the compound is administered after 24 hours of exposure. In another embodiment, the compound is administered after 36 hours of exposure. In another embodiment, the compound is administered within 48 hours of exposure. In another embodiment, the compound is administered within 60 hours of exposure. In another embodiment, the compound is administered within 72 hours of the exposure. In another embodiment, the compound is administered within 84 hours of the exposure.

In a certain embodiment or a particular formulation Yel002/BCN057 was solubalized in aqueous solution at physiologically compatible pHs using 100 mM methanesulfonic acid (MSA)/10% povidone (PVP); 100 mM MSA/2% benzyl alcohol/2% N-methylpyrrolidone (NMP); and, 100 mM MSA/10% ethanol/1% Poloxamer 188. In a further aspect 100 mM lactic acid was added and also improved solubility for these mixtures. In yet another embodiment, a formulation comprising Yel002 and 30 wt % Captisol (SBE-beta-CD) and 100 mM MSA yielded excellent solubility at up to pH 4.1 or higher.

In another embodiment formulation for intravenous, subcutaneous and oral delivery of therapeutic levels of Yel002/BCN057 were developed comprising 30 wt % Captisol (SBE-beta-CD) and 100 mM MSA at pH 4.1 or higher (adjusted with 1.0 N NaOH).

The disclosure now being generally described, it will be more readily understood by reference to the following examples which are included merely for purposes of illustration of certain aspects and embodiments of the present disclosure and are not intended to limit the disclosure.

Examples

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

BCN057 Mitigates RIGS and Improves Survival Following Lethal Dose of Radiation

Lethality from Acute Radiation Syndrome (ARS) depends upon dose dependent injury to various organs. Total body exposure to radiation dose higher than 8 Gy results in mortality within 15 days post exposure primarily due to RIGS. Intestinal epithelium is highly radio-sensitive because of its rapid self-renewal rate compared to any other organ. Every 4-5 days a new epithelium takes charge for mucosal defense under very strict epithelial homeostasis. High dose of radiation disrupts this homeostatic balance, kills ISCs and impairs the repair process resulting complete loss of mucosal barrier within 5-10 days post-exposure.

Figure 1A:
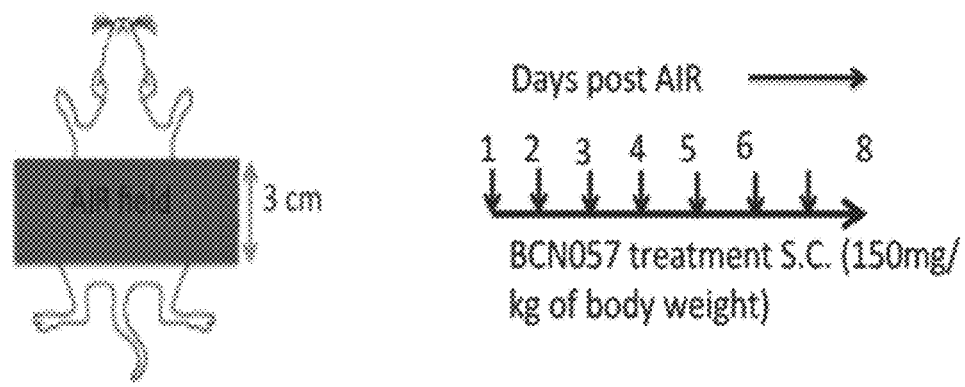
FIGS. 1A-1C: BCN057 treatment at 24 hrs post irradiation mitigates RIGS and improves survival in mice.
Figure 1B:
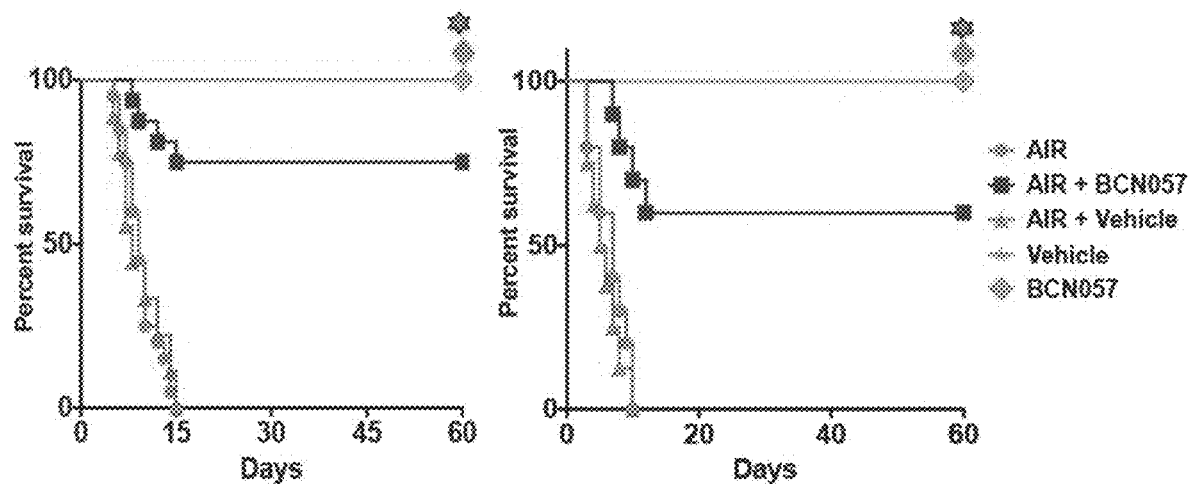

To examine the radio-mitigating role of BCN057 against RIGS, C57B16 mice were exposed to graded doses of abdominal irradiation (AIR) (14-15Gy) after shielding the thorax, head and neck, and extremities, thus protecting the bone marrow. A single fraction of 14-15 Gy AIR induces RIGS and lethality in 100% of animals within 7-12 days post-exposure. Mice receiving BCN057 at 24 hrs post AIR were continued survive beyond 30 days post-exposure without showing any symptoms of RIGS. These results clearly indicate that BCN057 mitigates the lethal radiation injury in intestine (FIGS. 1A and 1B).

Figure 1C:
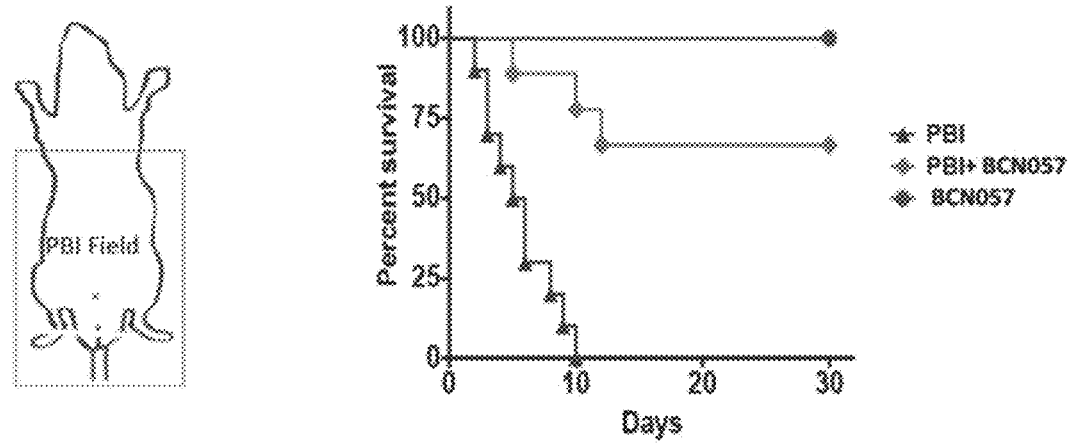

Unless there has been a very focal radiation exposure there will also be involvement of many other organ systems, and their differential responses to various doses of irradiation will impact the gastrointestinal acute radiation syndrome (GI-ARS) dose response. All radiation doses inducing GI-ARS will have a major impact on the bone marrow, which in turn will affect the levels of intestinal inflammation and ability of the body to manage the infection resulting from bacterial translocation through an impaired intestinal mucosal barrier. To investigate involvement of bone marrow in survival outcome upon BCN057 treatment, C57B16 mice were exposed to partial body irradiation (PBI) where 40% of total bone marrow was exposed (BM40) to irradiation after shielding head and fore limbs. Treatment with BCN057 at 24 hrs post exposure of 14.5 Gy PBI rescued 70% of mice from radiation lethality ($p<0.0001$). However, all the untreated mice were dead within 12 days post-exposure (FIG. 1C). This data indicated that BCN057 can rescue GI epithelium from GI epithelium even in absence of protective function from bone marrow (BM).

BCN057 treated mice were observed following AIR/PBI up to day 60 post exposure. These mice did not develop any clinical conditions indicating complete cure with BCN057 treatment.

Histo-pathological analysis of mice jejunum at 3.5 day to AIR clearly demonstrated loss of crypt with significant denudation of villus length indicating that RIGS is the primary cause of death. Mice receiving BCN057 treatment demonstrated normal crypt villus structure with an increase in number of crypts and preserved villous length. The percent of BrdU+ve crypt epithelial cells synthesizing DNA was significantly higher in BCN057 treated mice compared to untreated irradiated control (FIGS. 2A and 2C) ($p<0.0005$). However, treatment with BCN057 in non-irradiated mice did not induce any changes in crypt villus morphology and BRDU incorporation (FIGS. 2A, 2B and 2C).

Since dextran is unable to cross the GI epithelia unless it is compromised, dextran in the blood is a good indicator of epithelial damage. Blood FITC-dextran levels were measured at 4 h after gavage. Treatment with BCN057 significantly reduced the FITC-dextran uptake in the blood stream in irradiated mice compared untreated irradiated control mice (P<0.0005, unpaired t-test, two-tailed; FIG. 2B). These data indicate restitution of intestinal epithelial integrity by BCN057 treatment.

BCN057 Activates β-Catenin in Irradiated Jejunum

Intestinal epithelial self-renewal, homeostasis and repair are dependent upon WNT-β-catenin signaling. Activation of WNT-β-catenin signaling translocates β-catenin to nucleus to drive a gene expression program that supports ISC maintenance and proliferation. WNT activity of BCN057 was first examined by TCF/LEF reporter assay. Graded doses of BCN057 demonstrated significant increase in luciferase signal compared to vehicle control indicating WNT activity of BCN057 (FIGS. 7-9).

The effect of BCN057 was analyzed in crypt epithelial β-catenin activation. Immuno-histochemical analysis of jejunal sections from non-irradiated mice showed characteristic β-catenin with 40+5 cells being positive for nuclear β-catenin per 75 crypts (FIGS. 8 and 9). Mice exposed to AIR (20+2) had significantly fewer nuclear β-catenin positive cells compared to un-irradiated control. However, mice receiving BCN057 at 24 hrs post AIR demonstrated significant increase in nuclear β-catenin positive cells compared to irradiated untreated animals. Nuclear β-catenin positive cells were primarily observed in crypt bottom which is also location for ISCs indicating activation of WNT-β-catenin signaling in ISCs. Consistent with our immuno-histological staining of nuclear β-catenin expression the PCR array analysis of β-catenin target genes in crypt epithelial cells showed several fold increases in mRNA level in irradiated mice treated with BCN057 compared to irradiated control. Altogether these data indicate BCN057 activates the WNT-β-catenin signaling in irradiated crypt to induce crypt proliferation and regeneration.

BCN057 Rescues Lgr5+ISCs from Radiation Toxicity

Figure 10:
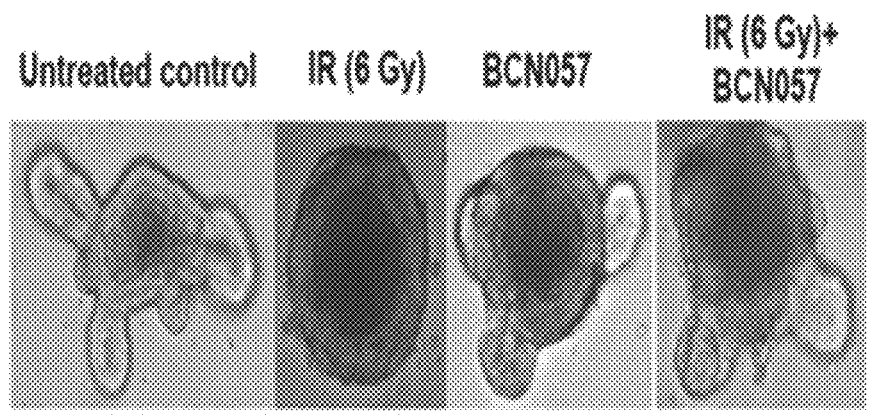

To analyze the effect of BCN057 on ISC population, an ex vivo primary intestinal culture system exposed to graded doses of irradiation was developed. Intestinal crypt isolated from Lgr5/EGFP-IRES-Cre-ERT2 knock in mice to allow the visualization of the ISCs. At a dose level of 8 Gy most of the Lgr5+ve ISCs had disappeared within 48 hrs resulting significant loss of budding crypt with changes in existing crypt morphology indicating inhibition of ISC growth and differentiation in response to radiation exposure. Treatment with BCN057 (10 uM) at 1 hr after irradiation rescued the organoids from radiation toxicity and restored the number of budding crypts to un-irradiated levels as represented by ratio of number of budding crypt/total crypt. A representative microscopic image of effect of BCN057 on budding crypt having Lgr5+ve ISCs (GFP+ve cells indicated with arrow) is shown in FIG. 10. In these microscopic observations over many experiments and analysis of crypts organoid we observed that BCN057 recused Lgr5+ve ISCs from 8Gy radiation toxicity.

To study this effect in vivo, the role of BCN057 in ISC survival was examined by exposing Lgr5/GFP-IRES-Cre-ERT2 knock-in mice to 15 Gy to AIR and then treated with BCN057. Lgr5+ve ISC had disappeared from crypt base within 48 hrs post AIR in untreated mice. However, irradiated mice receiving BCN057 showed significant preservation of Lgr5+ve ISC beyond 48 hrs post AIR (p<0.001) (FIGS. 11 and 12A). These results clearly indicate that BCN057 induces ISC self-renewal and proliferation in vitro and in vivo.

BCN057 Mitigates Radiation Injury in Human Colonic Epithelium Derived Organoid

To examine the effect of BCN057 on human intestinal, epithelial tissue surgical specimen collected from normal colon at least 10 cm apart from malignant site was used to develop ex vivo crypt organoid. At a dose level of 8 Gy all the budding crypts have been disappeared in the organoids. However, organoids treated with BCN057 at 1 hr post irradiation had budding crypts with complete restitution of organoid structure (FIG. 13). The effect of BCN057 on mRNA level of β-catenin target genes in organoids was also evaluated. Organoids exposed to irradiation and then treated with BCN057 demonstrated several fold increase in expression of β-catenin target genes indicating activation of WNT-β catenin signaling.

BCN057 does not Protect Malignant Tissue from Radiation

BCN057 was first examined in the National Cancer Institute (NCI) 60 cancer cell line platform. Several of these cell lines are known to be positive for dysregulation of the Wnt/b-catenin signaling pathway. None of these cells showed any proliferative response to BCN057 treatment. Next we examined the effect of BCN057 in human colonic tumor derived organoids exposed to irradiation. Treatment with BCN057 (10 uM) at 1 hr post radiation exposure (8Gy) did not recue organoids from radiation toxicity. As demonstrated in FIGS. 14 and 15 all the budding crypts disappeared within 72-96 hrs post irradiation in both BCN057 treated/untreated organoids.

Subcutaneous tumors were developed by injecting MC38 colon cancer cell in the flank. Mice with palpable, subcutaneous tumor were treated with AIR (16Gy) followed by eight doses of BCN057. AIR reduced the tumor growth but invariably produced 100% mortality of animals with a median survival time of 14+2 days. Compared to AIR alone, mice receiving BCN057 post AIR showed significant improvement in survival time. In AIR+BCN057 treated group 75% mice survived beyond 30 days and showed significant tumor growth retardation compared to untreated and non-irradiated control (p<0.0001) (n=10) (FIG. 16).

These results clearly indicate that radio-protective effect of BCN057 is specific for organoids derived from normal colon and therefore it can also be used as adjuvant therapy to minimize the toxic side effects of abdominal radiotherapy.

Discussion

Higher self-renewal rate of ISCs makes intestinal epithelium very sensitive to high dose of irradiation. Therefore, it is very critical to mitigate radiation induced gastro intestinal injury to overcome acute radiation syndrome. Present study indicates that treatment with BCN057 starting at 24 hrs post abdominal irradiation induced repair and regeneration of intestinal epithelium and improves survival against lethal doses of irradiation. Moreover, BCN057 also rescued mice from RIGS when 40% BM was exposed along with radiation to intestine which indicates that BCN057 can partially substitute the radio-protective role of BM in GI injury. BCN057 prevented Lgr5+ve ISCs from radiation induced loss and consequently mitigates RIGS.

This data has been replicated in intestinal organoid cultures from Lgr5-EGFP-Cre-ERT2 mice designed to examine the role of LGR5+ve ISCs in stem cell regeneration. This study along with the intestinal organoid culture developed from patient derived non-malignant colonic epithelium demonstrated that BCN057 induces the ISC regeneration. Intestinal epithelial homeostasis and regeneration depends upon the Wnt-β catenin signaling. BCN057 is a small molecular agent which activates Wnt-β catenin signaling as demonstrated in TCF/LEF luciferase assay as well as in irradiated crypt where it induces the nuclear localization of 0 catenin. These observations clearly indicate that BCN057 is an agonist of Wnt-β catenin signaling and can rescue the normal epithelial pathology with resultant survival of mice suggesting that this might be an effective mitigator of RIGS.

Intestinal crypts have two types of stem cells. Bmi1 positive ISCs that are long-lived, label-retaining stem cells present at the +4 position of the crypt base. These Bmi1+ve ISCs interconvert with more rapidly proliferating LRG5+ve stem cells known as crypt base columnar cells (CBCs) that express markers including Lgr5, Olfm4, Lrig1 and Asc12. These CBCs are also active stem cells, in as much as they are primarily involved in self-renewal and differentiation. Our previous observation demonstrated that activation of these stem cells post radiotherapy is critical for repair and regeneration of intestinal epithelium. We have also demonstrated that supplementation of WNT ligands is critical to activate WNT-β catenin signaling and rescue these stem cells following radiation injury. In the present study we have demonstrated that BCN057 as a single agent activates WNT-β catenin signaling and rescue these ISCs from radiation toxicity. Identification of suitable animal model to study RIGS and test the candidate agents as mitigators is still a major challenge as the mechanisms underlying this symptom may vary between models. So far multiple animal models has been used to study RIGS including mice, mini pig, canine and NHPs. However, there is no report on testing the radio-mitigators in human tissue.

In this study ex-vivo organoids were developed from colonic epithelium from human donors and demonstrated that BCN057 induces human colonic stem cell growth and proliferation following radiation. Intestinal organoids retain the crypt villus structure along with the all major cell types of intestinal epithelium including ISCs, paneth cells, enteroendocrine cells and enterocytes. Importantly, organoid growth primarily depends on the presence of stem cells Therefore, this organoid system provides a perfect platform to examine and validate the efficacy of any potential GI radiomitigators in human tissue. Another key point is to validate mechanistically the relationship between animal data and its translational value to human tissue with the response to BCN057 being the same in both.

The present study has also showed that BCN057 an anti-neoplastic agent does not have any radio-protective effect on organoids derived from human colon tumors or in mouse subcutaneous tumor. Therefore, during radiation therapy, systemic use of BCN057 may increase the therapeutic ratio in patients undergoing abdominal irradiation for GI malignancies. Several growth factors and cytokines such as KGF, TGFbeta, TNFα, PGE2, ILL including WNT agonist Rspondin1 have been shown to protect intestine from radiation or other cytotoxic injury by increasing the crypt cell proliferation and survival. But so far there are no reports of growth factors as mitigators of RIGS. This is the first demonstration of the salutary effect of BCN057 in the context of radiation injury of the intestine where it mitigates RIGS when applied 24 hrs after exposure to lethal doses of radiation.

Methods

Male C57Bl6/6J (Jackson laboratories) mice (five to six weeks old) were maintained ad libitum and all studies were performed under the guidelines and protocols of the Institutional Animal Care and Use Committee of the University of Kansas medical center.

Mice were injected subcutaneously with 1×105 MC38 (colon carcinoma cell line) cells on the flank, respectively. About 10 days later, the tumor became palpable (3-5 mm in diameter), whereupon abdominal irradiation 16 Gy was delivered. Mice were divided into 4 groups (n=10/group) receiving no treatment, AIR, BCN057 and BCN057 plus AIR. Animals received BCN057 eight times starting 24 hrs after AIR. Tumor measurements were performed thrice weekly using Vernier calipers along with simultaneous physical assessment of signs of systemic toxicity (malaise and diarrhea).

Irradiation Procedure

AIR was performed on anaesthetized mice (with a continuous flow 1.5 ml min-1 of 1.5% isoflurane in pure oxygen) using the small animal radiation research platform (SARRP, XStrahl, Surrey, UK). A 2 cm area of the mice containing the GI was irradiated (FIG. 2), thus shielding the upper thorax, head and neck as well as lower and upper extremities, protecting a significant portion of the bone marrow, thus inducing predominantly RIGS. A radiation dose of 14-15 Gy was delivered to the midline of the GI, ensuring homogeneous delivery by performing half of the total irradiation from the anterior-posterior direction and the second half from the posterior-anterior direction. The total irradiation time to deliver the intended dose was calculated with respect to dose rate, radiation field size and fractional depth dose to ensure accurate radiation dosimetry.

TCF/LEF (Topflash) Reporter Assay

To determine the canonical WNT activity of BCN057 HEK293 cells (Signosis, Santa Clara, Calif.) having TCF/LEF luciferase reporter construct were treated with BCN057 or vehicle control or PBS. LiCl (10 mM) treatment was used as positive control for luciferase activity. Luciferase activity was determined 24 hr after using Dual-Luciferase Reporter Assay System (Promega) as per manufacturer's protocol. HEK293 cells having FOPFLASH construct (mutated TCF/LEF-binding site) were used as negative control. HEK293 (human embryonic kidney) cell line was routinely characterized in the lab based on morphology and gene-expression patterns. Cells were confirmed to be free of *mycoplasma* contamination.

Histology

Since radiation doses>8 Gy induces cell cycle arrest and apoptosis of the crypt epithelial cells within day 1 post-radiation, resulting in a decrease in regenerating crypt colonies by day 3.5 and ultimately villi denudation by day 7 post-radiation exposure, animals were sacrificed when moribund or at 3.5 days after AIR for time course experiments and intestines were collected for histology. The intestine of each animal was dissected, washed in PBS to remove intestinal contents and the jejunum was fixed in 10% neutral-buffered formalin before paraffin embedding. Tissue was routinely processed and cut into 5 μm sections for haematoxylin and eosin and immunohistochemical staining. All haemotoxylin and eosin (HE) (Fisher Scientific, Pittsburgh, Pa.) staining was performed at the Pathology Core Facility in the KUMC Cancer Center.

Crypt Proliferation Rate

To visualize villous cell proliferation mid-jejunum was collected for paraffin embedding and Ki67 immunohistochemistry. Tissue sections were routinely deparaffinized and rehydrated through graded alcohols and incubated overnight at room temperature with a monoclonal anti Ki67 antibody. Nuclear staining was visualized using streptavidin-peroxidase and diaminobenzidine (DAB) and samples were lightly counterstained with haematoxylin. Murine crypts were identified histologically according to the criteria established by Potten et al. Digital photographs of crypts were taken at high (×20-60) magnification (Zeiss AxioHOME microscope) and crypt epithelial cells in intestinal sections were examined using ImageJ software and classified as Ki67 positive if they grossly demonstrated brown-stained nuclei from DAB staining or as Ki67 negative if they were blue stained nuclei. The proliferation rate was calculated as the percentage of KI67-positive cells over the total number of cells in each crypt. A total of 60 crypts were examined per animal.

Determination of Villi Length and Crypt Depth

Crypt depth was independently and objectively analyzed and quantitated in a blind manner from coded digital photographs of crypts from HE-stained slides using ImageJ 1.37 software to measure the height in pixels from the bottom of the crypt to the crypt villus junction. Villi length was determined by measuring the length from the crypt villus junction to villous tip. This measurement in pixels was converted to length (in μm) by dividing with the following a conversion factor (1.46 pixels μm-1).

β-Catenin Immunohistochemistry of Mouse Jejunum

β-Catenin immunohistochemistry was performed in paraffin-embedded sections of mouse jejunum (56). Before immunostaining antigen retrieval was performed by heating slides in pH 6.0 citrate buffer at 100° C. for 20 min in a microwave oven at 500 W using antigen retrieval solution (10 mM Tris and 1 mM EDTA, pH 9.0). Non-specific antibody binding was blocked for 20 min. by incubation with 0.05% w/v BSA in PBS. Tissue was stained using the anti-β-catenin antibody (1:100 dilution; BD Transduction Laboratories, Franklin Lakes, N.J.; #610154) at room temperature for 2 hr followed by staining with horseradish peroxidase-conjugated Anti-Mouse Antibody (Dako, Denmark) at room temperature for 1 hr. Peroxidase activity was detected by adding DAB substrate. Nucleus was counterstained with haematoxylin (blue). β-Catenin-positive nucleus (stained dark brown) was calculated from 15 crypts per field, 5 fields per mice.

Real-Time PCR to Determine 13-Catenin Target Genes mRNA Level

To compare the mRNA levels of β-catenin target genes in intestinal crypt cells from irradiated mice treated with BCN057 or PBS real-time PCR were performed using primer pairs for the genes Ephb2, Ascl, Olf, Tcf, Lef, Sox9 and Axin. RNA was isolated from crypt cells using RNeasy mini kit from Qiagen. Preparation of cDNA followed by real-time PCR array was performed according to manufacturer protocol (Qiagen).

FITC-Dextran Permeability Assay

At day 5 post mice exposed to ABI and/or treated with BCN057 were gavaged with 0.6 mg g-1 body weight of a FITC-dextran solution (4,000 kD size, Sigma). In all, four hrs. after gavage mice were killed and serum was obtained with cardiac puncture. Samples were measured in a 96-well plate using a Flexstation ii 384 multiwell fluorometer (Molecular Devices). A standard curve was constructed using mouse serum having increasing amounts of FITC-dextran to determine the serum levels of FITC-dextran in different treatment groups.

Preparation In Vitro Culture of Intestinal Crypt Organoids

Small intestine from Lgr5-GFP mice, or their littermates control mice was used for crypt isolation and development of ex vivo organoid culture. The tissue was scraped for removing villi and chopped into~5 mm pieces. Then tissue was washed with cold PBS, and incubated in dissociation buffer for 20 mins in rotor at room temperature. The tissue fragments were suspended vigorously with a 10-ml pipette in cold 0.1% BSA in PBS, yielding supernatants enriched in epithelial cells. Samples were passed through 100 μm filters (BD Biosciences) to obtain Fraction 1. Same step was repeated thrice to get fraction 2, 3 and 4. Fraction 3 and fraction 4 enriched in crypt stem cells were centrifuged at 300 g for 5 min at 4° C. and diluted with advanced DMEM/F12 (Invitrogen) containing B27, N2, 1 μM n-Acetylcysteine, 10 mM HEPES, penicillin/streptomycin, and Glutamax (all Invitrogen). Samples were passed through 100 μm filters (BD Biosciences), and centrifuged at 275 g for 5 min at 4° C. and single cells were discarded. Crypts were embedded in extracellular matrix (BD Bioscience) and seeded on pre-warmed 24-well plate. After the matrix solidified, Intesticult medium (Stem Cell Technologies, Inc.) with supplements and gentamycin (50 ug/ml) was overlaid. Passage was performed at day 7. The number of organoids per well was counted on microscopic images. The images of organoids were acquired using fluorescent microscopy (Nikon, 80i) and confocal microscope (Nikon, A1RMP). Total number of crypt structures and number of budding crypts were counted and expressed as a ratio of budding crypts/total crypt structure.

NCI Cancer 60 Cancer Cell Line Screen

100 μL of each cell preparation was tested in accordance with its particular type and density, ranging from 5000-40,000 cells per well in a 96-well microtiter plate, corresponding to their own growth rate. BCN057 was evaluated 10 uM and incubation for 48 hours in a 5% CO2 atmosphere with 100% humidity. Proliferation was assayed using the sulforhodamine B assay with a plate reader to read the optical densities.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the present disclosure to be practiced otherwise than specifically described herein. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present disclosure (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the disclosure otherwise claimed. No language in the present specification should be construed as indicating any non-claimed element essential to the practice of the disclosure.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present disclosure, which is defined solely by the claims. Accordingly, the present disclosure is not limited to that precisely as shown and described.

The invention claimed is:

1. A method of treating radiation or chemotherapy induced damage to epithelial cells in a subject in need thereof, the method comprising the step of administering to the subject a therapeutically effective amount of a compound of Formula I:

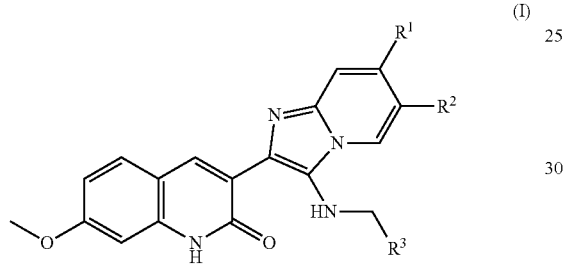

wherein $R^1$ and $R^2$ are independently selected from the group consisting of hydrogen, amino, amide, F, Cl, Br, I, nitro, alkoxy, hydroxyl, thiol, alkylthio, acyl carboxylic acid, ester, sulfonyl, sulfonamide, —SO$_4$H, optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, and optionally substituted phenyl; and wherein $R^3$ is optionally substituted $C_1$-$C_{20}$ alkyl, optionally substituted $C_1$-$C_{20}$ alkenyl, optionally substituted $C_1$-$C_{20}$ alkynyl, optionally substituted cycloalkyl, optionally substituted cycloalkenyl, optionally substituted heterocycloalkyl, optionally substituted heteroaryl, or optionally substituted phenyl wherein the radiation or chemotherapy induced damage to epithelial cells is identified as one or more of radiation-induced gastrointestinal syndrome (RIGS), chemotherapy-induced gastrointestinal syndrome, radiation-induced mucositis, chemotherapy-induced mucositis, radiation-induced oral mucositis, chemotherapy-induced oral mucositis, radiation-induced proctitis, chemotherapy-induced proctitis, chemotherapy-induced enteritis or radiation-induced enteritis.

2. The method of claim 1, wherein the compound is administered to the subject within 48 hours of radiation exposure.

3. The method of claim 1, wherein the compound is administered to the subject after 24 hours of radiation exposure.

4. The method of claim 1, wherein the analog is selected from the group consisting of Formula IE-IH,

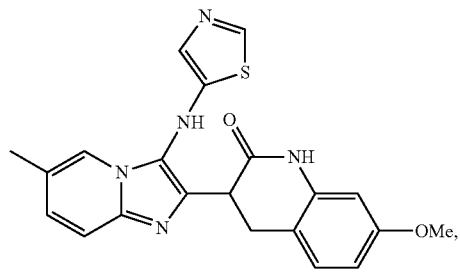

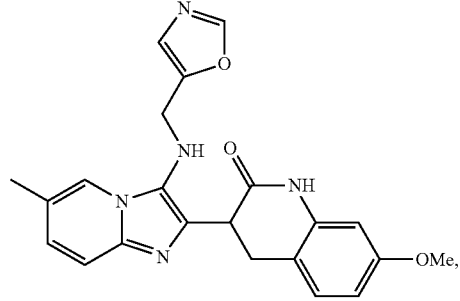

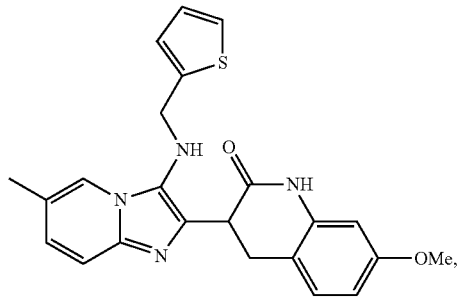

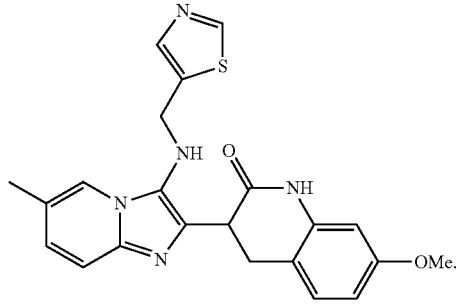

5. The method of claim 1, wherein the compound is Formula IA

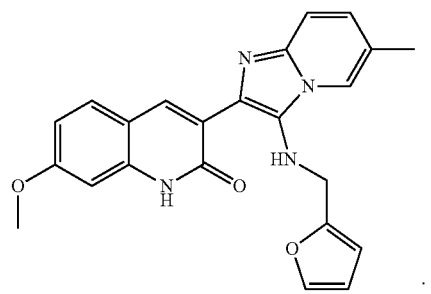

6. The method of claim 1, wherein the subject received radiation therapy.

* * * * *